US 8,822,229 B2

(12) United States Patent
Wakitani et al.

(10) Patent No.: US 8,822,229 B2
(45) Date of Patent: Sep. 2, 2014

(54) METHOD FOR ASSAYING KERATAN SULFATE, ASSAY KIT THEREFOR AND METHOD FOR DETECTING JOINT DISEASE BY USING THE SAME

(75) Inventors: Shigeyuki Wakitani, Osaka (JP); Hiroshi Fujita, Tokyo (JP); Takeshi Ishimaru, Tokyo (JP); Koji Yamamoto, Kanagawa (JP); Yasuhiro Kurahashi, Kanagawa (JP); Junichi Onaya, Tokyo (JP); Hiroyuki Masuda, Tokyo (JP)

(73) Assignee: Seikagaku Corporation, Tokyo (JP)

( * ) Notice: Subject to any disclaimer, the term of this patent is extended or adjusted under 35 U.S.C. 154(b) by 160 days.

(21) Appl. No.: 13/142,262

(22) PCT Filed: Dec. 24, 2009

(86) PCT No.: PCT/JP2009/071395
§ 371 (c)(1),
(2), (4) Date: Sep. 14, 2011

(87) PCT Pub. No.: WO2010/074123
PCT Pub. Date: Jul. 1, 2010

(65) Prior Publication Data
US 2011/0318759 A1    Dec. 29, 2011

(30) Foreign Application Priority Data

Dec. 26, 2008  (JP) ................... 2008-332642
Aug. 7, 2009   (JP) ................... 2009-185244

(51) Int. Cl.
*G01N 33/564* (2006.01)

(52) U.S. Cl.
USPC ........ 436/509; 435/7.1; 435/7.94; 435/287.2; 436/518; 436/539; 436/540

(58) Field of Classification Search
USPC ............... 435/7.1, 7.94, 287.2; 436/509, 518, 436/539, 540
See application file for complete search history.

(56) References Cited

U.S. PATENT DOCUMENTS 4,704,356 A    11/1987    Thonar

FOREIGN PATENT DOCUMENTS

| EP | 2 128 615 A1 | 12/2009 |
| WO | 90/07120 A1 | 6/1990 |
| WO | 2008/096738 A1 | 8/2008 |

OTHER PUBLICATIONS

Tibor T. Glant, et al., "Monoclonal antibodies to different protein-related epitopes of human articular cartilage proteoglycans", Biochem. J., 1986, pp. 31-41, 234.

(Continued)

*Primary Examiner* — Melanie Y Brown
*Assistant Examiner* — Erik B Crawford
(74) *Attorney, Agent, or Firm* — Sughrue Mion, PLLC

(57) ABSTRACT

The inventions provides a method for immunologically determining a keratan sulfate level which method includes bringing an anti-keratan sulfate monoclonal antibody into contact with a biological sample, the anti-keratan sulfate monoclonal antibody exhibiting a relative reaction specificity between keratan sulfate-I and keratan sulfate-II represented by $IC50^{KS-I/KS-II}$ of 0.4 to 5, to thereby provide a signal; and detecting keratan sulfate contained in the biological sample from the signal. On the basis of the method, the invention also provides a joint disease detection method and a method for assessing the effect of a remedy for a joint disease and a candidate substance therefor. Through these methods, a very small amount of keratan sulfate contained in a sample, can be determined. Particularly, these methods can determine, at high-sensitivity and high-specificity, the total keratan sulfate including keratan sulfate-I, which have been difficult to determine through a conventional technique. The methods also enables detect a joint disease and assess the effect of a remedy for a joint disease or a candidate substance therefor.

7 Claims, 11 Drawing Sheets

(56) References Cited

OTHER PUBLICATIONS

C. Anthony Poole, et al., "Chondrons from Articular Cartilage. (IV) Immunolocalization of Proteoglycan Epitopes Isolated Canine Tibial Chondrons", The Journal of Histochemistry and Cytochemistry, 1991, pp. 1175-1187, vol. 39, No. 9.

Laszlo Kopper, et al., "Proteoglycan-targeted antibodies as markers on non-Hodgkin lymphoma xenografts", Cancer Immunol Immunother, 1990, pp. 137-142, 32.

Seikagaku Biobusiness Corporation: "Material safety data sheet: Anti-Keratan sulfate [BCD-4]", Anonymous, Oct. 12, 2007, Retrieved from the Internet: URL:http://www.acciusa.com/pdfs/MSDS_ns/270429m.pdf [retrieved on Jun. 29, 2012].

CHEMICON International, Inc.: "Mouse Anti-Oligosaccharide Associated Epitope of Cartilage Proteoglycan Monoclonal Antibody", anonymous, Dec. 20, 1999, Retrieved from the Internet: URL:http://www.millipore.com/publications.nsf/a73664f9f981af8c852569b9005b4eee/defbcc3a20bd9f358525730600738a4a/$FILE/MAB2025.pdf [retrieved on Jun. 29, 2012].

CHEMICON International, Inc.: "Mouse Anti-Corneal Keratan Sulfate Monoclonal Antibody", anonymous, Dec. 16, 1999, retrieved from the Internet: URL:http://www.millipore.com/publications.nsf/a73664f9f981af8c852569b9005b4eee/91aefe4b7b68b97185257306007388ef/$FILE/MAB2020.pdf [retrieved on Jun. 29, 2012].

CHEMICON international, Inc.: "Mouse Anti-Proteoglycan Monoclonal Antibody". Anonymous, Dec. 1998, Retrieved from the Internet: URL:http://www.millipore.com/publications.nsf/a73664f9f981af8c852569b9005b4eee/60feddcl4c34b49185257306007383b9/$FILE/MAB2005.pdf [retrieved on Jun. 29, 2012].

Extended European Search Report for Application 09834921.0-1223/2386857 dated Jul. 31, 2012.

Glant et al.; Age-related changes in protein-related epitopes of human articular-cartilage proteoglycans; Biochem. J. (1986) vol. 236, pp. 71-75.

Thonar et al.; Quantification of Keratan Sulfate in Blood as a Marker of Cartilage Catabolism; Arthritis and Rheumatism; vol. 28, No. 12, Dec. 1985; pp. 1367-1376.

Thonar et al.; Serum Keratan Sulfate—A Marker of Predisposition to Polyarticular Osteoarthiritis; Clinical Biochemistry, vol. 25, Jun. 1992; pp. 175-180.

Office Action issued in Japanese Patent Application No. 2009-554803, dated Feb. 25, 2014.

Office Action issued in counterpart European Patent Application No. 09834921.0 dated Apr. 9, 2013.

METHOD FOR ASSAYING KERATAN SULFATE, ASSAY KIT THEREFOR AND METHOD FOR DETECTING JOINT DISEASE BY USING THE SAME

CROSS REFERENCE TO RELATED APPLICATIONS

This application is a National Stage of International Application No. PCT/JP2009/071395 filed Dec. 24, 2009, the contents of which are incorporated herein by reference in their entirety.

TECHNICAL FIELD

The present invention relates to a method for determining a very small amount of keratan sulfate contained in a sample at high sensitivity and high specificity and to a kit for use in the method. The invention further relates to a method for detecting a joint disease employing the determination method, to a kit for use in the detection method, to a method for assessing the effect of a remedy for a joint disease or a candidate substance therefor, and to a kit for assessing the effect.

BACKGROUND ART

Keratan sulfate is a glycosaminoglycan and is present as a side chain of proteoglycan or keratan sulfate proteoglycan such as aggrecan, keratocan, or lumican, in limited tissues such as cartilage and the cornea. Keratan sulfate is an acidic polysaccharide having, as a basic sugar chain structure, a disaccharide recurring structure formed of N-acetyl-D-glucosamine and D-galactose, and sulfated with various degrees. In the cornea, keratan sulfate is an important component for maintaining transparency thereof, and in cartilage, keratan sulfate is an aggrecan component serving as an important extracellular matrix for maintaining the structure of cartilage. Particularly, since serum keratan sulfate levels of patients of joint diseases such as osteoarthritis and rheumatoid arthritis are known to vary, keratan sulfate is a candidate substance as a marker for diagnosing joint diseases.

Keratan sulfate is categorized into keratan sulfate-I, originating from the cornea and mackerel skin, and keratan sulfate-II, originating from cartilage, intervertebral disks, and pulpous nuclei. The mode of bonding of keratan sulfate to the core protein varies between keratan sulfate-I and keratan sulfate-II. In keratan sulfate-I, an aspartic acid residue is bonded to a sugar chain via N-glycoside bonding, while in keratan sulfate-II, a serine or threonine residue is bonded to N-acetylgalactosamine via O-glycoside bonding (Seikagaku Jiten (3rd edition), published by Tokyo Kagaku Dojin). Regarding the structural features of keratan sulfate, keratan sulfate-I has a main structure including four saccharide moieties and three sulfate groups, and keratan sulfate-II has a main structure including four saccharide moieties and four sulfate groups. That is, keratan sulfate-I has a sulfate content lower than that of keratan sulfate-II.

One known antibody against such keratan sulfate is 5D4 (name of clone). The antibody is known to recognize (or bind), as a minimum recognition unit, a structure including five sulfate groups with respect to six saccharide molecules (Non-Patent Document 1) and to react with a keratan sulfate having a relatively high sulfate content. This antibody is commercially available from Seikagaku Corporation and is widely employed in research.

Examples of currently employed keratan sulfate detection methods include cellulose acetate membrane electrophoresis, high-performance liquid chromatography (HPLC), and immunological assay (e.g., ELISA). Due to poor sensitivity, cellulose acetate membrane electrophoresis is disadvantageous for the detection of a micro-amount of keratan sulfate in a sample. One known HPLC method is a method by Miyauchi et al. (Patent Document 1). In such an HPLC method, keratan sulfate contained in the sample is digested by keratanase, which specifically decomposes keratan sulfate, and the formed disaccharide is analyzed. Although the HPLC method exhibits high specificity and higher sensitivity, the sample must be subjected to preliminary treatments such as digestion by protease, crude purification, and digestion by keratanase, generally making this method disadvantageous for the treatment of a large number of samples. The ELISA method is suitable for the treatment of a large number of samples and is highly operable. Examples of known ELISA techniques include a competitive ELISA method employing 5D4 (Patent Document 2), and the sandwich ELISA method employing 5D4 (Patent Document 3).

The competitive ELISA method, which employs only one type of antibody, exhibits low specificity in the assay system in some cases, and is thought to be affected by a substance co-existing in the sample. Thus, the sandwich ELISA method exhibits higher specificity. The keratan sulfate assay method through sandwich ELISA employing 5D4 is useful for the detection of keratan sulfate in a sample. Actual measurement results obtained through the assay have been reported for a serum or synovial fluid of humans, dogs, horses, and rabbits, and a synovial fluid of guinea pigs. However, there have been virtually no reports on the assay of rat-derived and mouse-derived samples, which are thought to contain a very small amount of keratan sulfate. Thus, even at present, keratan sulfate assay encounters difficulty, and there are many biological samples in which the presence of keratan sulfate is undetermined.

PRIOR ART DOCUMENTS

Patent Documents

Patent Document 1: Japanese Patent Application Laid-Open (kokai) No. 2001-57900
Patent Document 2: Japanese Patent Publication (kokoku) No. 1994-84971
Patent Document 3: WO 90/07120

Non-Patent Documents

Non-Patent Document 1: Eur. J. Biochem., 157, 385-491 (1987)

SUMMARY OF THE INVENTION

Problems to be Solved by the Invention

Objects of the present invention are to provide a method for determining a very small amount of keratan sulfate contained in a sample, more particularly, such a determination method which enables high-sensitivity and high-specificity determination of the total keratan sulfate including keratan sulfate-I, which has been difficult to determine through a conventional technique, and a kit employed in the method; a method for detecting a joint disease employing the determination method; a detection kit for use in the detection method; a method for assessing the pharmaceutical effect of a remedy for a joint disease or a candidate substance therefor; and a kit for assessing the effect.

Means for Solving the Problems

The present inventors have carried out extensive studies for attaining the aforementioned objects in consideration of reaction specificity of an antibody to keratan sulfate, and have found that a very small amount of keratan sulfate contained in a sample can be determined at high sensitivity and high specificity in a simple manner by use of an anti-keratan sulfate antibody which sufficiently reacts with keratan sulfate-I, having a low sulfate content, and with keratan sulfate-II, having a high sulfate content, and which exhibits a small difference between reaction specificity to keratan sulfate-I and that to keratan sulfate-II. The present invention has been accomplished on the basis of this finding.

Accordingly, the present invention provides a method for immunologically determining a keratan sulfate level comprising:

bringing an anti-keratan sulfate monoclonal antibody into contact with a biological sample, the anti-keratan sulfate monoclonal antibody exhibiting a relative reaction specificity between keratan sulfate-I and keratan sulfate-II represented by $IC50^{KS-I/KS-II}$ of 0.4 to 5, to thereby provide a signal; and detecting keratan sulfate contained in the biological sample from the signal (hereinafter the method may be referred to as "the determination method of the present invention").

In the determination method, $IC50^{KS-I/KS-II}$ represents a value obtained through dividing a 50% inhibition keratan sulfate-I concentration (ng/mL) obtained in a predetermined competitive immunological determination method by a 50% inhibition keratan sulfate-II concentration (ng/mL) obtained in the predetermined competitive immunological determination method. The terms "50% inhibition keratan sulfate-I concentration obtained in a predetermined competitive immunological determination method" and "50% inhibition keratan sulfate-II concentration (ng/mL) obtained in a predetermined competitive immunological determination method" respectively refer to concentrations determined through the method described in Example 1 given hereinbelow. As described in Example 1, commercial products of keratan sulfate-I and keratan sulfate-II, i.e., KS(BC) (available from Seikagaku Corporation) and KPS-1 (products of Seikagaku Corporation) may be employed. These keratan sulfate products generally have the following characteristics.

KS-I: disaccharide analysis: (Gal6S-GN6S)/total=36 to 44%
  GPC analysis: 13 kDa to 15 kDa
KS-II: disaccharide analysis: (Gal6S-GN6S)/total=95 to 100% GPC analysis: 12 kDa to 14 kDa The above analytical data may be obtained through the following methods (1) and (2), described hereinbelow along with specific results of the measurement.

(1) Disaccharide Compositional Proportions in KS-I and Those in KS-II

The compositional proportions of
2-acetamido-2-deoxy-4-O-(β-D-glucopyranosyl)-6-O-sulfo-D-gulcose (Gal-GN6S) and
2-acetamido-2-deoxy-4-O-(6-O-sulfo-β-D-glucopyranosyl)-6-O-sulfo-D-gulcose (Gal6S-GN6S) were determined through HPLC according to the method disclosed in "Analytical method to determine keratan sulfate in the serum using HPLC. Kurahashi Y, Masuda H, Miyazaki K. Rinsho Byori (2008) 56(5), 373-378." Table 1 shows the results. Each proportion is represented as a ratio of the amount of each component to the total amount of the two disaccharide units.

TABLE 1

Disaccharide proportions in KS-I and KS-II

| KS | Lot | Gal-GN6S (%) | Gal6S-GN6S (%) |
| --- | --- | --- | --- |
| KS-I | A | 57.9 | 42.1 |
|  | B | 59.8 | 40.2 |
|  | C | 59.2 | 40.8 |
| KS-II | A | 1.2 | 98.8 |
|  | B | 2.3 | 97.7 |
|  | C | 3.3 | 96.7 |

(2) Analysis of Molecular Weights of KS-I and KS-II

The molecular weight of KS-I and that of KS-II were determined through GPC according to the method described in "Identification and functions of chondroitin sulfate in the milieu of neural stem cells. Ida M, Shuo T, Hirano K, Tokita Y, Nakanishi K, Matsui F, Aono S, Fujita H, Fujiwara Y, Kaji T, Oohira A., J. Biol. Chem. (2006) 281(9), 5982-5991." Five chondroitin sulfate species, which molecular weights had been determined through the method disclosed in "Evaluation of Molecular Weights of Hyaluronate Preparations by Multi-Angle Laser Light Scattering. Chikako Yomota Bull. Natl. Health Sci. (2003) 121, 030-033" were employed as analytical standards. Table 2 shows the results. The molecular weight is represented as a peak molecular weight.

TABLE 2

Molecular weights of KS-I and KS-II

| KS | Lot | Molecular weight (kDa) |
| --- | --- | --- |
| KS-I | A | 13,837 |
|  | B | 14,157 |
| KS-II | A | 13,432 |
|  | B | 12,834 |

The biological sample is preferably a blood sample or a synovial fluid. The term "blood sample" includes, for example, serum, plasma, or whole blood, etc.

Examples of the "anti-keratan sulfate monoclonal antibody exhibiting an $IC50^{KS-I/KS-II}$ of 0.4 to 5" include BCD-4, BCD-7, BC-261, BC-703, MK-172, MK-202, and EFG-11 (described hereinbelow).

In one preferred embodiment of the determination method of the present invention, there is used a solid-phased anti-keratan sulfate antibody in which an anti-keratan sulfate antibody is immobilized onto a solid-phase support or a labeled anti-keratan sulfate antibody in which a labeling substance is bonded to an anti-keratan sulfate antibody.

One exemplary keratan sulfate immunological determination method includes the following steps:

[step 1] a step of bringing, into contact simultaneously or sequentially with a biological sample, a solid phase to which an anti-keratan sulfate monoclonal antibody has been immobilized, the anti-keratan sulfate monoclonal antibody exhibiting a relative reaction specificity between keratan sulfate-I and keratan sulfate-II represented by $IC50^{KS-I/KS-II}$ of 0.4 to 5, and a labeled form of the antibody, to thereby form, on the solid phase, an immune complex of the antibody and keratan sulfate contained in the biological sample; and

[step 2] a step of determining the keratan sulfate level of the biological sample from a detected value obtained from a label signal of the immune complex.

In one preferred embodiment of the determination method of the present invention, the solid-phased anti-keratan sulfate antibody and the labeled anti-keratan sulfate antibody may be derived from the same anti-keratan sulfate antibody or from anti-keratan sulfate antibodies that are different from each other.

The present invention also provides a kit for carrying out the aforementioned determination method of the present invention; i.e., a keratan sulfate assay kit for use in determination of the level of keratan sulfate present in a sample through an immunological determination method, the kit comprising, as an anti-keratan sulfate monoclonal antibody, a monoclonal antibody selected from the group consisting of BCD-4, BCD-7, BC-261, BC-703, MK-172, MK-202, and EFG-11 (hereinafter the kit may be referred to as "the assay kit of the present invention").

The present invention also provides the aforementioned assay kit of the present invention, wherein the monoclonal antibody is a combination of BCD-4 and MK-172 or a combination of BCD-7 and EFG-11.

The present invention also provides a method for detecting a joint disease comprising the following steps (hereinafter the method may be referred to as "the disease detection method of the present invention"):

[step 1] a step of determining the keratan sulfate level of a test specimen through the determination method of the present invention;

[step 2] a step of comparing the keratan sulfate level of the test specimen determined by step 1 with the keratan sulfate level of a normal specimen and/or keratan sulfate levels of the test specimen determined through a plurality of measurements with an interval or intervals; and

[step 3] a step of assessing the joint disease, on the basis of the comparison of step 2, as positive when the keratan sulfate level of the test specimen is higher than the keratan sulfate level of the normal specimen, or as progressive when the keratan sulfate level of the test specimen determined by one measurement among said measurements is higher than the level determined in the preceding measurement.

Similar to the determination method of the present invention, the disease detection method of the present invention enables assessment of a joint disease particularly when the test specimen is a blood specimen (the same meaning as blood sample) or synovial fluid.

Examples of the joint disease include osteoarthritis and traumatic arthropathy. The disease detection method of the present invention can easily detect deformation features of an osteoarthritis which cannot be detected by an X-ray examination.

As used herein, the term "deformation features of an osteoarthritis which cannot be detected by an X-ray" refers to a state in which radiological findings of the diagnosis of arthrosis according to the method by Kellgren and Lawrence (Ann. Rheum. Dis. 1957, 16, 494-502) include Grade 0 or Grade I state and some conditions such as pain and swelling are observed and in which deterioration or damage of the articular cartilage such as change in color tone, fibrilar feature, or fissuring are observed under an articular endoscope.

The present invention also provides a detection kit for carrying out the aforementioned disease detection method of the present invention; the kit comprising, as an anti-keratan sulfate monoclonal antibody, a monoclonal antibody selected from the group consisting of BCD-4, BCD-7, BC-261, BC-703, MK-172, MK-202, and EFG-11 (hereinafter the kit may be referred to as "the joint disease detection kit of the present invention").

The present invention also provides the aforementioned joint disease detection kit, wherein the monoclonal antibody comprises a combination of BCD-4 and MK-172 or a combination of BCD-7 and EFG-11.

The present invention also provides a method for assessing the therapeutic effect of a remedy for a joint disease or a candidate substance therefor, characterized in that the method comprises the following steps (hereinafter the method may be referred to as "the remedy effect assessing method of the present invention"):

[step 1] a step of determining the keratan sulfate level of a test specimen through the determination method of the present invention before and after administration, to a subject, of the joint disease remedy or a candidate substance therefor (hereinafter may be referred to as "remedy or the like");

[step 2] a step of comparing the keratan sulfate level of the test specimen before administration of the remedy or the like with the keratan sulfate level of the test specimen after administration thereof, the levels having been determined in step 1; and

[step 3] a step of detecting, on the basis of the comparison in step 2, the extent of a change in keratan sulfate level, said change being from the keratan sulfate level before administration of the remedy or the like to that level after administration thereof, to see whether there is any tendency toward a normal level, to thereby assess the effect of the remedy or the like based on the extent of the change as an index.

The present invention also provides a kit for carrying out the aforementioned method for assessing the pharmaceutical effect on a joint disease; the kit comprising, as an anti-keratan sulfate monoclonal antibody, a monoclonal antibody selected from the group consisting of BCD-4, BCD-7, BC-261, BC-703, MK-172, MK-202, and EFG-11 (hereinafter the kit may be referred to as "the pharmaceutical effect assessing kit of the present invention").

The present invention also provides the aforementioned pharmaceutical effect assessing kit of the present invention, wherein the monoclonal antibody is a combination of BCD-4 and MK-172 or a combination of BCD-7 and EFG-11.

As used herein, the term "immunological determination method" refers to all the methods employing antigen-antibody reaction and is the same as immunoassay. The term "competitive immunological determination method" refers to a method including causing a substance to be determined (test antigen) to be present in a system containing a labeled antigen and an antibody, to thereby react the labeled antigen and the test antigen with the antibody in a competitive or inhibitive manner; performing B/F separation through an appropriate technique; and measuring a signal of the labeling substance. The term "sandwich method" refers to a method including forming an immune complex from a solid-phased antibody, an antigen, and a labeled antibody in an assay system; performing B/F separation through an appropriate technique; and measuring a signal of the labeling substance. That is, the sandwich method is a non-competitive immunological determination method employing a solid phase (immunometric assay). Among these methods, such a method employing an enzyme as a labeling substance is called a sandwich ELISA method. The term "protease" refers to a protein-degrading enzyme (proteolytic enzyme, peptide hydrolase) and is a collective term of enzymes which can break peptide bonding. The details of the definitions of these terms are disclosed in, for example, "Biotechnology Jiten, published by CMC (1989)" or "Seikagaku Jiten (3rd edition) (1989)."

Effects of the Invention

Through employment of the determination method and assay kit of the present invention, keratan sulfate-I, which has been difficult to determine, can be detected at high sensitivity, whereby a very small amount of keratan sulfate in a biological sample can be detected at high sensitivity and specificity in a simple manner. According to the invention, a very small amount of keratan sulfate present in a variety of animal samples, which has been difficult to detect, can be specifically detected, whereby keratan sulfate in a variety of samples can be detected. As a result, in the biological and medical fields, particularly in articular studies, development of the related pharmaceuticals and diagnostic reagents become possible on the basis of evidence obtained from animal models or in vitro models. Thus, the invention enables provision of very useful test tools for research and development and diagnosis.

According to the disease detection method and detection kit of the present invention, variation in microlevel of keratan sulfate in a test specimen is correlated with a joint disease, whereby a new useful index for a joint disease is provided. Such variation has not been detected through a conventional technique. Specifically, damage of cartilage in the knee joint or other joints can be detected at high sensitivity. Furthermore, the pharmaceutical effect assessing method and assessing kit of the present invention enable assessment of the established effect of a remedy for a joint disease in the clinical setting and the effect of a candidate substance of a remedy for a joint disease through screening by detecting the keratan sulfate level in a test specimen at high sensitivity.

MODES FOR CARRYING OUT THE INVENTION

Figure 1:
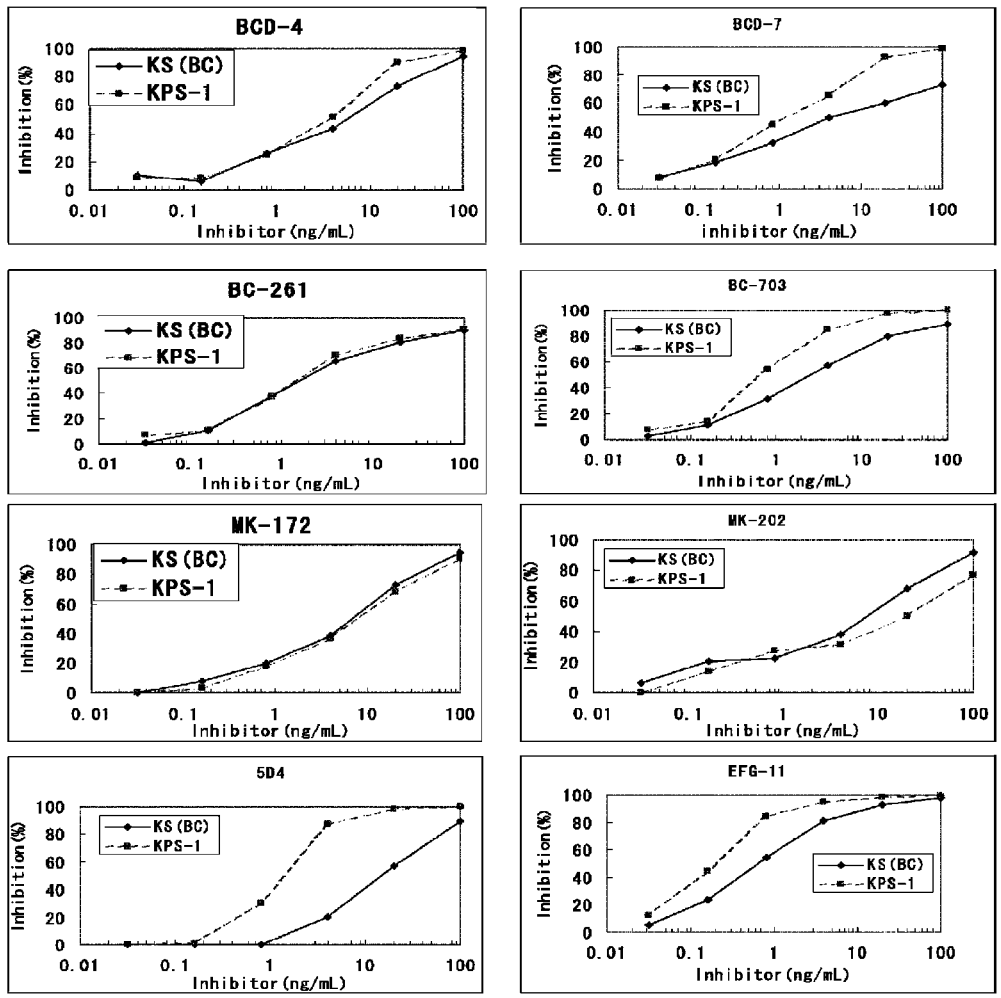
FIG. 1 shows the results of study on reactivity of each anti-keratan sulfate antibody with keratan sulfate-I or II.

The present invention will next be described in more detail.
[Determination Method and Kit]
A characteristic feature of the determination method of the present invention resides in that the anti-keratan sulfate monoclonal antibody employed in the method sufficiently reacts with two keratan sulfate species; i.e., keratan sulfate-I (hereinafter may be referred to as KS-I) and keratan sulfate-II (hereinafter may be referred to as KS-II), and exhibits a small difference between reaction specificity to KS-I and that to KS-II, that is, the relative reaction specificity between KS-I and KS-II represented by $IC50^{KS-I/KS-II}$ is 0.4 to 5, preferably 0.4 to 3.8. As mentioned above, the "$IC50^{KS-I}$" refers to a KS-I concentration at which 50% of the reaction of the anti-keratan sulfate antibody with a biotin-labeled KS-I is inhibited by KS-I in competitive immunological assay (e.g., competitive ELISA), and the "$IC50^{KS-II}$" refers to a KS-II concentration at which 50% of the reaction of the anti-keratan sulfate antibody with a biotin-labeled KS-I is inhibited by KS-II.

No particular limitation is imposed on the method of producing the anti-keratan sulfate antibody exhibiting a small difference between reaction specificity to KS-I and that to KS-II, so long as the aforementioned antibody can be provided, and any known method may be appropriately employed for the production. For example, the antibody can be produced by use of an antigen (a matrix component derived from the cartilage, the cornea, etc.; proteoglycan, or keratan sulfate proteoglycan such as aggrecan, lumican, or keratocan; or purified keratan sulfate or a keratan sulfate derivative) through a technique such as in vivo immunization, in vitro immunization, cell technology, or genetic engineering technique (J. of Biological Chemistry 258, 8848-8854 (1993), Biochem. J., 234, 31-41 (1986)).

Specifically, the anti-keratan sulfate antibody exhibiting a small difference between reaction specificity to KS-I and that to KS-II which antibody may be employed in the determination method of the present invention may be produced by producing a hybridoma which produces the antibody, and culturing the hybridoma or proliferating the hybridoma in the body of an animal. Alternatively, the target antibody may be genetically produced through the phage display technique by use of mRNA obtained from antibody-producing cells.

The production of the anti-keratan sulfate monoclonal antibody employed in the determination method of the present invention essentially includes the following steps: (1) immunization of a heterologous animal with an immunogen such as human articular cartilage; (2) separation of antibody-producing cells from the heterologous animal; (3) cell fusion of the antibody-producing cells and myeloma cells; (4) selection of a hydridoma; (5) proliferation of the hybridoma; and (6) separation and purification of the antibody.

(1) Immunization

The immunogen employed in the invention is preferably cartilage, proteoglycan, keratan sulfate proteoglycan, aggrecan, or a digested or undigested product thereof with chondroitinase A or ABC. The animal species from which the immunogen is derived may be any of bovine, horse, sheep, goat, rat, mouse, guinea pig, dog, pig, rabbit, monkey, dove, chicken, etc. In particular, human and comparatively large animals such as bovine and pig are preferred. The immunogen is preferably prepared from a material which is a tissue containing an immunogen such as the cornea and articular cartilage taken from the aforementioned animals.

No particular limitation is imposed on the heterologous animal (non-human animal) to which the immunogen is administered, so long as the animal is different from the animal from which the immunogen was derived, and any of bovine, horse, sheep, goat, rat, mouse, guinea pig, dog, pig, rabbit, monkey, dove, chicken, etc. may be employed. Particularly, mouse, rat, guinea pig, rabbit, goat, sheep, etc. are preferably employed. Among them, mouse (BALB/c) is the most generally employed animal for immunization.

Administration of the immunogen to such animals may be carried out through a routine method. In one exemplary procedure, a suspension of the immunogen in an adjuvant is prepared, and the suspension is intravenously, intraperitoneally, hypodermally, or intradermally administered, or administered to the planta, the spleen, or the lymph nodes. Examples of the adjuvant include Freund's complete adjuvant, Freund's incomplete adjuvant, alum adjuvant, aluminum hydroxide adjuvant, *Bordetella pertussis* adjuvant, TiTer Max, Titer Max Gold, and RIBI adjuvant system.

The amount of the immunogen administered to the animal is appropriately predetermined in accordance with the type of the immunization animal, the immunization injection site, etc. When the immunization animal is a mouse, the immunogen amount is preferably about 0.01 to about 10 mg/mouse.

After completion of the first immunization, booster is performed once to about five times with intervals of 1 to 4 weeks in a similar manner, whereby production of the antibody to keratan sulfate is induced in the animal body.

The antibody titer of the serum of the immunization animal is repeatedly determined through ELISA or a similar technique. When the antibody titer has reached the target level, the immunogen is dissolved in an adjuvant, physiological saline (0.9% aqueous sodium chloride solution or PBS), etc., and the solution is intravenously or intraperitoneally administered, or administered to the spleen, the planta, etc., to thereby complete the final immunization.

(2) Separation of Antibody-Producing Cells from Heterologous Animal

Antibody-producing cells such as splenic cells, lymph node cells, and peripheral blood lymphocytes are taken from an immunized animal through a routine method. The antibody-producing cells taken from the animal are preferably splenic cells or lymph node cells.

(3) Fusion of Antibody-Producing Cells and Myeloma Cells

The myeloma cells which are to be fused with the antibody-producing cells (in this section, the cells refer to splenic cells or lymph node cells obtained after immunization) are cells of an established cell line derived from human or a variety of animals such as mouse and rat, which cells generally available by those skilled in the art. Preferably, the cell line employed has drug resistance and cannot be live in a selection medium in an unfused state but can live only in a fusion state with the antibody-producing cells. Typically, an 8-azaguanine-resistant strain is employed. The cell strain, having a defect of hypoxanthine guaninephosphoribosyl transferase, cannot grow in a hypoxanthine-aminopterin-thymidine (HAT) medium. Preferably, the cell strain does not secrete immunoglobulin; i.e., the cell strain is of a non-secreting type.

Specific examples of the myeloma cell strain include mouse myeloma cell strains such as P3x63Ag8 (ATCC TIB-9) (Nature, 256495-497 (1975)), P3x63Ag8U.1 (P3-U1) (ATCC CRL-1597) (Current Topics in Microbiology and Immunology, 81, 1-7 (1978)), P3x63Ag8.653 (ATCC CRL-1580) (J. Immunology. 123. 1548-1550 (1979)), P2/NSI/1-Ag4-1 (ATCC TIB-18) (European J. Immunology. 6, 511-519 (1976)), Sp2/O-Ag14 (ATCC CRL-1581) Nature, 276, 269-270 (1978)); rat myeloma cell strains such as 210.RCY.Ag1.2.3 (Y3-Ag1.2.3) (ATCC CRL-1631) (Nature 277, 131-133 (1979)); and human myeloma cell strains such as U-266-AR1 (Proc. Natl. Acad. Sci. U.S.A., 77, 5429 (1980)), GM1500 (Nature, 288, 488 (1980)), and KR-4 (Proc. Natl. Acad. Sci. U.S.A., 79, 6651 (1982)).

In the cell fusion, a myeloma cell which is adapted to the antibody-producing cell is selected. In order to effectively perform cell fusion, myeloma cells and antibody-producing cells are mixed at a ratio of 1:(1 to 10) in an animal cell culture medium such as an Eagle's minimum essential medium (MEM), a Dulbecco's modified Eagle medium (DMEM), or a RPMI-1640 medium at $10^6$ to $10^8$ cells/mL and two members are brought into contact with each other at 37° C. for 1 to 10 minutes. For promoting cell fusion, a fusion-promoting agent such as polyethylene glycol (PEG) having an average molecular weight of 1,000 to 6,000, poly(vinyl alcohol), or Sendai virus may be employed. Alternatively, the antibody-producing cells may be fused with the myeloma cells by means of a commercial cell fusion apparatus employing electric pulse.

For selecting a hybridoma of interest from the cells after completion of cell fusion, the hybridoma may be subjected to selective proliferation. In one specific procedure, a cell suspension is appropriately diluted with, for example, a RPMI-1640 medium containing 10 to 20% fetal calf serum (FCS), and the cells are seeded on a microplate at about $10^3$ to about $10^6$ cells (as the number of antibody-producing cells)/well. A selection medium (e.g., HAT medium) is added to each well, and cultivation is performed while the medium is renewed at an appropriate timing. In the case where 8-azaguanine-resistant cell strain is employed as the myeloma cell, and an HAT medium is employed as a selection medium, unfused myeloma cells die on about day 7 to about day 14 of cultivation. Also, the antibody-producing cells; i.e., normal cells, cannot grow for a long time in vitro. Thus, cells which grow after day 7 to day 14 may be recovered as hybridomas.

(4) Selection of Hybridoma (Screening)

A hybridoma that produces a keratan sulfate-recognizing antibody may be retrieved through enzyme immunoassay (EIA, ELISA), radio-immunoassay (RIA), etc. In one procedure, keratan sulfate or a keratan sulfate derivative is immobilized on the solid phase of a 96-well ELISA microplate, and a culture supernatant containing the monoclonal antibody is added to the microplate, whereby the antibody produced by the hybridoma is reacted with keratan sulfate. Then, an enzyme-labeled anti-immunoglobulin antibody is reacted with the bound specific antibody. In an alternative procedure, a biotin-labeled anti-immunoglobulin antibody is reacted, followed by enzyme-labeled avidin or streptavidin. Subsequently, in each case, a corresponding enzyme substrate is added to each well for coloring. Among the candidates, a culture supernatant which has colored only in a keratan sulfate-immobilized well is selected, to thereby select a hybridoma that produces an antibody which reacts specifically with keratan sulfate (screening).

The selected hybridoma(s) may be cloned through limiting dilution, the soft agar method, the fibrin gel method, the fluorescence excitation cell sorter method, etc.

(5) Proliferation of Hybridoma

The thus-recovered hybridoma may be proliferated to produce the target antibody through a generally employed cell culturing method or ascites formation method, or a similar method.

In one mode of cell culturing, the hybridoma is cultured in an animal cell culture medium such as a 10 to 20% FCS-containing RPMI-1640 medium or a serum-free medium through a routine culturing method or a high-density culturing method, and the antibody is recovered from the culture supernatant.

In recovering ascites, a mineral oil such as pristane (2,6,10,14-tetramethylpentadecane) is intraperitoneally administered to an animal whose tumor tissue is identical with the hybridoma. Then, for example, in the case of mouse, hybridoma is intraperitoneally administered at about $10^6$ to about $10^7$ cells/mouse. The hybridoma forms an ascites tumor on about day 7 to about month 1, whereby a large amount of the target antibody is produced in serum and ascites of the animal. The thus-formed ascites is recovered.

(6) Separation/Purification of Antibody

If required, the target antibody may be purified from a culture supernatant, ascites, etc. containing the antibody through appropriately selected and combined known techniques such as ammonium sulfate precipitation, ion-exchange chromatography employing an anion-exchanger such as DEAE cellulose, affinity chromatography employing protein A-Sepharose or the like, molecular sieve chromatography, and other techniques.

Alternatively, commercial antibodies may also be employed. Although the type of the aforementioned antibody is not limited to a monoclonal antibody, a polyclonal antibody, etc., a monoclonal antibody is preferred from the viewpoint of specificity. For example, there may be employed monoclonal antibodies disclosed in Biochem. J. (1986) 234, 31-41, in vivo 4: 149-152 (1990), Cancer Immunol. Immunother. (1990) 32: 132-142, Biochem. J. (1986) 236, 71-75, The Journal of Histochemistry and Cytochemistry. Vol. 39, No. 9, pp. 1175-1187 (1991), and ARTHRITIS & RHEUMATISM. Vol. 38, No. 5, pp. 660-668 (1995).

Examples of the aforementioned anti-keratan sulfate monoclonal antibody include EFG-11, BCD-4, BCD-7, BC-261, BC-703, MK-172, and MK-202 (clones of the monoclonal antibody).

All of the above anti-keratan sulfate monoclonal antibodies exhibit a reaction specificity between KS-I and KS-II represented by $IC50^{KS-I/KS-II}$ of 0.4 to 5; i.e., a small difference between reaction specificity to KS-I and that to KS-II, as shown in Example 1 (Table 4) described hereinbelow.

These anti-keratan sulfate monoclonal antibodies have the following general characteristics.

1) EGF-11 (Cosmo Bio Co., Ltd. and CHEMICON INTERNATIONAL INC., catalogue No.: MAB2022)
Immunogen: human articular cartilage proteoglycan digested by chondroitinase ABC
Immunization animal: mouse
Antibody class: IgG2b
Cross animal species: human, mouse, bovine, dog, pig, and sheep
Specificity: recognizing the 2-3 disaccharide unit of keratan sulfate chain (non-bonded or proteoglycan-bonded form) originating from the skeleton (Type I) and from the cornea (Type II)

2) BC-261 (Cosmo Bio Co., Ltd. and CHEMICON INTERNATIONAL INC., catalogue No.: MAB2020)
Immunogen: keratan sulfate proteoglycan originating from the bovine cornea
Immunization animal: mouse
Cross animal species: human, bovine
Antibody class: IgG1
Specificity: reacting with a protein-related epitope present in keratan sulfate proteoglycan originating from the human or bovine cornea and in high-density cartilage proteoglycan 3) BC-703 (Cosmo Bio Co., Ltd. and CHEMICON INTERNATIONAL INC., catalogue No.: MAB2025)
Immunogen: keratan sulfate proteoglycan originating from the bovine cornea
Immunization animal: mouse
Cross animal species: human, bovine
Antibody class: IgG3
Specificity: reacting with a protein-related epitope bonding to O-bound oligosaccharide of cartilage or cornea proteoglycan of a variety of animals 4) MK-172 (Cosmo Bio Co., Ltd. and CHEMICON INTERNATIONAL INC., catalogue No.: MAB2005)
Immunogen: fetal human articular cartilage digested by chondroitinase A
Immunization animal: mouse
Cross animal species: human, bovine, dog
Antibody class: IgG3
Specificity: recognizing a protein-related epitope bonding to a bonding domain of a chondroitin sulfate chain of high-density cartilage proteoglycan of various species 5) MK-202
Immunogen: fetal human articular cartilage digested by chondroitinase A
Immunization animal: mouse
Antibody class: IgG1
Specificity: recognizing a protein-related epitope bonding to a bonding domain of a chondroitin sulfate chain of high-density cartilage proteoglycan of various species 6) BCD-4
Immunogen: human articular proteoglycan A1D1 fraction and/or human proteoglycan digested by chondroitinase ABC
Immunization animal: mouse
Antibody class: IgG1
Specificity: recognizing a peptide moiety to which keratan sulfate or a keratan sulfate-like structure of a proteoglycan monomer is bonded 7) BCD-7
Immunogen: human articular proteoglycan A1D1 fraction and/or human proteoglycan digested by chondroitinase ABC
Immunization animal: mouse
Antibody class: IgG1
Specificity: recognizing a moiety which is susceptible to cutting by pronase or papain or through alkali treatment and which has no keratan sulfate, chondroitin sulfate, or oligosaccharide According to the present invention, an anti-keratan sulfate antibody having a newly found reaction specificity is employed. Specifically, there is employed an anti-keratan sulfate antibody which sufficiently reacts with keratan sulfate-I, having a low sulfate content, and with keratan sulfate-II, having a high sulfate content, and which preferably exhibits a small difference between reaction specificity to KS-I and that to KS-II. The present invention employing the antibody has first realized specific determination of a very small amount of keratan sulfate contained in a sample, in particular the total amount of keratan sulfate including keratan sulfate-I, which has been difficult to determine through a conventional method.

Among the aforementioned monoclonal antibodies, mouse-mouse hybridoma BCD-4 was domestically deposited as a hybridoma cell line producing BCD-4, and mouse-mouse hybridoma MK-172 was domestically deposited as a hybridoma cell line producing MK-172, at the International Patent Organism Depositary, National Institute of Advanced Industrial Science and Technology (1-1, Higashi 1-chome, Tsukuba-shi, Ibaraki, Japan) under Deposition Nos. FERM P-21364 and FERM P-21365, respectively, on Sep. 13, 2007. Then, they were transferred to the international deposit under Budapest Treaty under Deposition Nos. FERM BP-11210 and FERM BP-11211, respectively, received on Dec. 15, 2009.

Among the aforementioned monoclonal antibodies, mouse-mouse hybridoma EFG-11 was domestically deposited as a hybridoma cell line producing EFG-11 at the International Patent Organism Depositary under Deposition No. FERM P-21741 on Dec. 3, 2008. Then, it was transferred to the international deposit under Budapest Treaty under Deposition No. FERM BP-11212 received on Dec. 15, 2009. Furthermore, mouse-mouse hybridoma BCD-7 was domestically deposited as a hybridoma cell line producing BCD-7 at the International Patent Organism Depositary under Deposition No. FERM P-21773 on Feb. 17, 2009. Then, it was transferred to the international deposit under Budapest Treaty under Deposition No. FERM BP-11213 received on Dec. 15, 2009.

The determination method of the present invention employs the aforementioned antibody and determines the keratan sulfate level of a sample through an immunological assay method. Examples of the immunological assay method include a competitive method and a sandwich method. Of these, sandwich method is preferred, from the viewpoint of specificity.

Among such competitive methods and sandwich methods, those employing an enzyme as a labeling substance (competitive ELISA and sandwich ELISA) are preferred, from the viewpoint of operability.

When the determination method of the present invention involves a sandwich method, a conventionally employed technique, procedure, etc. may be basically employed. In one exemplary procedure, an anti-keratan sulfate antibody is immobilized onto a solid-phase support, and then a sample which may contain keratan sulfate is added to the antibody, followed by reaction under certain conditions (e.g., ambient temperature (15 to 25° C.) for 20 to 120 minutes), to thereby form a complex ("solid-phased anti-keratan sulfate antibody-keratan sulfate") between "solid-phased anti-keratan sulfate antibody" and "keratan sulfate." Subsequently, a labeled anti-keratan sulfate antibody in which a labeling substance for detecting keratan sulfate in "solid-phased anti-keratan sulfate antibody-keratan sulfate" has been bonded to an anti-keratan sulfate antibody is added to the complex and the mixture is allowed to stand or stirred under certain conditions (e.g., ambient temperature (15 to 25° C.) for 20 to 120 minutes), to thereby form an immune complex ("solid-phased anti-keratan sulfate antibody-keratan sulfate-labeled anti-keratin sulfate antibody") between "solid-phased anti-keratan sulfate antibody-keratan sulfate" and "labeled anti-keratan sulfate antibody." Subsequently, solid-liquid phase separation (B/F separation) is performed, and the signal attributed to the labeling substance in the solid phase or that in the liquid phase is measured. The thus-obtained signal may be employed as an index for quantitation or detection of keratan sulfate contained in the sample. Alternatively, in the exemplary procedure, keratan sulfate which may be contained in the sample is reacted with the labeled anti-keratan sulfate antibody, to thereby form an immune complex with "keratan sulfate-labeled anti-keratan sulfate antibody," and then the solid-phased anti-keratan sulfate antibody is reacted with the liquid phase containing the immune complex, to thereby form "solid-phased anti-keratan sulfate antibody-keratan sulfate-labeled anti-keratan sulfate antibody" immune complex. Thereafter, solid-liquid phase separation is performed. In a further alternative procedure, keratan sulfate which may be contained in the sample, the solid-phased anti-keratan sulfate antibody, and the labeled anti-keratan sulfate antibody are caused to be co-present in the same reaction system, to thereby form "solid-phased anti-keratan sulfate antibody-keratan sulfate-labeled anti-keratan sulfate antibody" immune complex. Thereafter, solid-liquid phase separation is performed.

In other words, when the determination method of the present invention is performed through the sandwich ELISA technique, one characteristic feature of the determination method resides in that simultaneously or sequentially reacting, with a biological sample, (1) a solid-phased anti-keratan sulfate antibody in which an anti-keratan sulfate antibody has been immobilized and (2) a labeled anti-keratan sulfate antibody in which a labeling substance has been bonded to the corresponding anti-keratan sulfate antibody, to thereby form an immune complex from the keratan sulfate in the sample, (1), and (2); performing solid-liquid phase separation; measuring a signal attributed to the labeling substance in the solid phase or liquid phase; employing the signal as an index for quantitation or detection of keratan sulfate in the biological sample.

When the determination method of the present invention is performed through the competitive ELISA technique, one possible embodiment of determining the keratan sulfate level of a biological sample includes the following:

immobilizing keratan sulfate or an anti-keratan sulfate antibody on a solid-phase support; adding a biological sample and a labeled anti-keratan sulfate antibody or labeled keratan sulfate to which a labeling substance has been bonded; and detecting, through the aforementioned technique, the labeling substance of the labeled anti-keratan sulfate antibody or labeled keratan sulfate which has been competitively bound to the keratan sulfate or the anti-keratan sulfate antibody immobilized on a solid-phase support.

As described above, the anti-keratan sulfate antibody immobilized on a solid-phase support has an $IC50^{KS-I/KS-II}$ value of 0.4 to 5, preferably 0.4 to 3.8. Specific examples of the antibody include EFG-11, BCD-4, BCD-7, BC-261, BC-703, MK-172, and MK-202, which are described above.

The anti-keratan sulfate antibody forming the labeled anti-keratan sulfate antibody also has an $IC50^{KS-I/KS-II}$ value of 0.4 to 5, preferably 0.4 to 3.8. Specific examples of the antibody include EFG-11, BCD-4, BCD-7, BC-261, BC-703, MK-172, and MK-202, which are described above.

More specific examples of the combination of the solid-phased anti-keratan sulfate antibody and the labeled anti-keratan sulfate antibody will be described. In the case where a sample derived from the below-described small animal such as guinea pig, rat, mouse, or rabbit is assayed in terms of keratan sulfate, the anti-keratan sulfate antibody is more preferably selected from BCD-4 and MK-172, since keratan sulfate in a variety of biological samples can be detected at higher sensitivity, as mentioned in the Examples hereinbelow. Most preferably, BCD-4 is employed as a solid-phased anti-keratan sulfate antibody, and MK-172 is employed as a labeled anti-keratan sulfate antibody.

In the case where a human-derived sample is assayed in terms of keratan sulfate, more preferably, EFG-11 or BCD-7 is employed as a solid-phased anti-keratan sulfate antibody, and BCD-7 or EFG-11 is employed as a labeled anti-keratan sulfate antibody.

No particular limitation is imposed on the solid-phase support onto which the anti-keratan sulfate antibody is immobilized, so long as it can immobilize the antibody. Examples of the solid-phase support include a plate, a tube, balls, beads, membrane, latex, gel, and magnetic microparticles. Among them, a plate, balls, beads, latex, and a plate are preferred. A plate, in particular, a microplate having a plurality of wells, is more preferred, since a number of specimens can be simultaneously assayed in a more simple manner. Examples of the material of the solid-phase support include glass, ceramic, silicone rubber, polystyrene, polyvinyl chloride, polypropylene, nylon, acrylic resin, and rubber.

The anti-keratan sulfate antibody or keratan sulfate may be immobilized onto the aforementioned solid-phase support through a method generally employed as a immobilized enzyme preparation method such as the physical adsorption method, the covalent bond method, or the entrapping immobilization method (see Immobilized enzyme, 1975, published by Kodansha, p. 9 to 75). Of these, the physical adsorption method is preferred from the viewpoint of simple operation.

In the immobilization, the anti-keratan sulfate antibody may be bonded to the solid-phase support directly or by the mediation of another substance.

In one direct immobilization method, an anti-keratan sulfate antibody is dissolved in a buffer having a pH of about 7 to about 9 (e.g., phosphate buffer, phosphate buffered saline (PBS), or carbonate buffer), and the solution is added to a solid-phase support (e.g., wells of a microplate), followed by storage at about 37° C. for 1 to 2 hours or at about 4° C. for one night. In order to prevent non-specific bonding of keratan sulfate or other molecular species contained in a sample to the surface of the solid-phase support, a blocking agent is preferably added to the thus-obtained solid-phased anti-keratan sulfate antibody so as to cover the area where the anti-keratan sulfate antibody is not immobilized. Examples of the blocking agent which may be employed include animal-derived serum albumin, casein, and milk protein; vegetable-derived protein; and hydrolyzed products thereof (peptides). Commercial blocking agents such as Applie Duo (available from Seikagaku Corporation) may also be employed. In one mode of blocking, a blocking agent such as Applie Duo or bovine serum albumin is added to the solid-phase support, and the support is allowed to stand at about 37° C. for 30 minutes to 2 hours, or maintained at ambient temperature (15 to 25° C.) for 1 to 2 hours, to thereby cover the area of the solid-phase support where the anti-keratan sulfate antibody is not immobilized. In the case of a blocking agent which can be applied to an antibody-immobilized dry plate such as Applie Duo, the plate is dried at 35 to 40° C. after sufficient removal of the blocking solution, to thereby produce an anti-keratan sulfate antibody-immobilized plate of interest.

Preferably, after binding of keratan sulfate contained in the sample to the anti-keratan sulfate antibody immobilized onto the solid-phase support, the surface of the solid-phase support is washed with a washing liquid, to thereby remove non-specifically adsorbed matter. Examples of the washing liquid which may be employed in the invention include buffers (e.g., phosphate buffer, phosphate buffered saline (PBS), and Tris-HCl buffer) to which a surfactant such as a Tween surfactant is added.

Examples of the labeling substance bonded to the anti-keratan sulfate antibody employed for detection include enzymes such as peroxidase, alkaline phosphatase, β-galactosidase, luciferase, acetylcholinesterase, micro-peroxidase, glucose oxidase, glucose-6-phosphate dehydrogenase, and malate dehydrogenase; radioisotopes such as [$^{125}$I], [$^{131}$I], [$^{3}$H], [$^{99m}$Tc], and [$^{14}$C]; fluorescent substances such as coumarin, naphthylamine, and fluorescein isothiocyanate (FITC); chemiluminescent substances such as luminol and isoluminol; hapten; biotin; and avidin (e.g., streptavidin). However, the labeling substance is not particularly limited to the above examples, and those which can generally label protein may be employed.

As used herein, the term "labeling substance" also includes a substance such as biotin, which is not directly detected and employed in detection in combination with another substance (e.g., avidin) which is specifically bound the substance such as biotin and to which a detectable labeling substance is bound.

The aforementioned antibody may be labeled through a known method suitable for the labeling substance employed. For example, in the case of labeling of an enzyme, the glutaraldehyde method, the periodic acid crosslinking method, the maleimide crosslinking method, the carbodiimide method, the activated ester method, etc. may be employed. In the case of labeling with a radioisotope, the chloramine T method, the lactoperoxidase method, etc. may be employed (see Biochemistry Laboratory Guide 2, 2nd series, "Chemistry of Protein (part 2)," published by Tokyo Kagaku Dojin, 1987). Alternatively, labeling may be performed by means of a commercial kit, for example, a peroxidase labeling kit (product name: Quick Labeler-Pro NH$_2$, available from Seikagaku Corporation).

The method of detecting a labeling substance; i.e., the method of measuring a signal attributed to the labeling substance, which varies depending on the labeling substance employed, will next be described. When biotin is employed as a labeling substance, in one embodiment of the detection method, an enzyme to which streptavidin or the like has been bound is added, and the enzyme (e.g., peroxidase) is bound to an immune complex including biotin as a labeling substance via streptavidin or the like. Then, a coloring substrate such as tetramethylbenzidine (i.e., substrate to the enzyme) and a hydrogen peroxide solution are added. The degree of coloration of the enzymatic reaction product is measured as absorbance. When a fluorescent substance or a chemiluminescent substance is employed as a labeling substance, in one embodiment of the detection method, the fluorescence or luminescence of the solution after reaction is measured.

In the determination method of the present invention, the keratan sulfate level of the sample may be determined by drawing a calibration curve between the keratan sulfate level and the intensity of the signal attributed to the labeling substance by use of a keratan sulfate standard solution having a known keratan sulfate concentration, and comparing the signal of a concentration-unknown specimen with the calibration curve.

No particular limitation is imposed on the biological sample employed in the determination method of the present invention, so long as the sample may contain keratan sulfate. Examples of the sample include synovial fluid, blood, serum, plasma, urine, bone marrow aspirate, and extract of a tissue (e.g., cartilage or cornea) derived from human and other animals. Among them, as described above, blood samples and synovial fluid are preferred.

Examples of preferred samples derived from non-human animals include those derived from a small animal such as guinea pig, rat, mouse, or rabbit.

Through subjecting to protease treatment the biological sample employed in the determination method of the present invention, precision of the determination can be further enhanced. In biological samples, keratan sulfate is bound to the core protein of aggrecan, whereas the keratan sulfate standard sample is not bound to the core protein. Thus, the bond between keratan sulfate and the core protein of aggrecan is cut in advance through protease treatment of the biological sample, to thereby reduce difference in condition between keratan sulfate in the sample and the keratan sulfate standard sample, whereby the precision of the determination method of the present invention can be further enhanced. No particular limitation is imposed on the protease employed in the treatment. However, the protease employed preferably has low reaction specificity to the substrate protein, does not affect the stability of keratan sulfate, and has an optimum pH range which is approximately a neutral pH range that less affects the determination. Examples of preferred proteases include pronase, subtilisin, papain, and trypsin. Of these, pronase and subtilisin are particularly preferred, with pronase being most preferred. Pronase is a protease produced by Actinomycetes (*Streptomyces griseus*), and examples of commercial products thereof include Actinase series (Actinase E, A, AS, AF: Kaken Pharmaceutical Co., Ltd.), pronase (product of Sigma-Aldrich, catalogue No.: P9811), and pronase (product of Roche). The proteases may be used singly or in combination of two or more species. When two or more species thereof are employed, at least one species is preferably pronase. Needless to say, protease is preferably reacted with the biological sample in the vicinity of enzymatic optimal conditions such as the optimum pH and the optimum temperature thereof. No particular limitation is imposed on the amount of protease employed, which amount varies depending on the properties and titer of the employed protease, so long as the employed protease sufficiently separates keratan sulfate from the core protein of aggrecan. Since those skilled in the art can easily determine the specific amounts of respective proteases employed in the treatment, no excessive trials are required to be performed for determining the amount. A specific example of the amount determination procedure is described in the Example.

The assay kit of the present invention for determining the keratan sulfate level is provided for the purpose of performing the aforementioned determination method, and preferably contains at least one species selected from among the aforementioned anti-keratan sulfate antibodies, specifically, EFG-11, BCD-4, BCD-7, BC-261, BC-703, MK-172, and MK-202.

The same specific combinations of the solid-phased anti-keratan sulfate antibody and the labeled anti-keratan sulfate antibody as described above may also be employed as preferred combinations.

In addition to the aforementioned non-labeled and/or labeled antibody, if required, the assay kit of the present invention may further contain additional elements appropriately selected from among a concentration-known keratan sulfate standard sample for use as a standard for drawing a calibration curve, a labeling-substance-detecting reagent, an anti-keratan sulfate antibody-labeling reagent, the aforementioned blocking agent, the aforementioned washing liquid, a specimen-diluting liquid, an enzymatic reaction-terminating liquid, etc. The essential configuration of the assay kit of the present invention is the same as that of the detection kit of the present invention and that of the assessing kit of the present invention. However, the detection kit or the assessing kit of the present invention preferably contains an element which realizes effective detection of a joint disease or effective assessment of the effect of a test remedy, such as an assay manual including measurement data of standard keratan sulfate levels of healthy subjects obtained from a test specimen through the determination method of the present invention.

[Detection of Disease]

As described above, the determination method of the present invention enables quantitation or detection of keratan sulfate in a specimen at high sensitivity in a simple manner. Thus, through application of the determination method to specimens of a human or other animals, a joint disease can be detected mainly on the basis of the determination results as indices.

Accordingly, as described above, the disease detection method of the present invention is directed to a method for detecting a joint disease, the method comprising the following three steps:

1) a step of determining the keratan sulfate level of a test specimen through the determination method of the present invention (first step);

2) a step of comparing the keratan sulfate level of the test specimen determined by the first step with the keratan sulfate level of a normal specimen and/or keratan sulfate levels of the test specimen determined through a plurality of measurements with an interval or intervals (second step); and 3) a step of assessing the joint disease, on the basis of the comparison of the second step, as positive when the keratan sulfate level of the test specimen is higher than the keratan sulfate level of the normal specimen, or as progressive when the keratan sulfate level of the test specimen determined by one measurement among said measurements is higher than the level determined in the preceding measurement (third step).

In the first step, examples of the test specimen include synovial fluid, blood specimens (serum, plasma, and whole blood), and urine samples. Among them, the synovial fluid recovered from a diseased part or a serum or plasma sample is preferably employed. The method of collection and treatment of the specimen is performed through a routine procedure. The subject from which the specimen is obtained is a human and another animal whose joint disease is to be examined and treated. Hereinafter, the disease detection method of the present invention will be described, taking a human subject as an example. However, the disease detection method may be applied in substantially the same manner to non-human animal subjects.

The "keratan sulfate level of a normal specimen" in the second step may be the keratan sulfate level of a specimen taken from a test specimen-donor when the donor was in healthy condition, and, strictly speaking, this keratan sulfate level is preferred. However, in an actually employed assay method, the averaged keratan sulfate level of specimens of healthy subjects is preferably employed. This averaged keratan sulfate level is obtained by collecting, from specimens of a plurality of healthy subjects, keratan sulfate level measurements determined though the determination method of the present invention and averaging the thus-obtained keratan sulfate levels. The average value may be obtained at a national or regional level or a medical center level. If many volunteers participate in the trial, those skilled in the art can readily calculate the average value without making excessive efforts.

The expression in the third step "the keratan sulfate level of the test specimen is higher than the keratan sulfate level of the normal specimen" refers to the state in which the keratan sulfate level of the test specimen is clearly higher as compared with the keratan sulfate level of the normal specimen.

Notably, as shown in the Examples hereinbelow, in the case of joint inflammation, the keratan sulfate level of synovial fluid and that of a blood specimen determined through the determination method of the present invention are high.

Particularly, whether or not the cartilage has been damaged can be assessed through the disease assessing method of the present invention. Among knee joint diseases, osteoarthritis is one typical disease possibly accompanied by the damage of cartilage. Osteoarthritis is categorized into a primary type, in which no specific cause is found, and a secondary type, which is caused by a precedent causal disease. Causes of the secondary type include congenital (e.g., varus/valgus deformation), traumatic (e.g., fracture or meniscus lesions), endocrine (e.g., obesity), and rheumatic disease. Generally, cartilage plays a primary role in absorbing shock and providing lubrication in the joint tissue. By virtue of the structure including cartilage, the joint can be smoothly moved for a long period of time without wearing the related bones. However, in osteoarthritis, cartilage cells, which synthesize collagen (elastic fibrillary protein forming the connective tissue) and proteoglycan (substance providing elasticity) forming the cartilage tissue, are disordered, whereby synthesis of collagen and proteoglycan is inhibited. Thus, the surface of the joint cartilage, which per se is smooth, is roughened with a large number of small dents. As a result, in such a state, external shock cannot be absorbed by the cartilage. In this case, all the members forming the joint; i.e., bone, articular capsule, synovial membrane tissue, tendon, ligament, etc., are deformed.

In the most severe case, the case involves difficulty in walking. However, in an early stage of cartilage damage, in many cases no severe pain is sensed; i.e., the patient does not sense the cartilage damage. When the cartilage damage is sensed, the damage is very severe, and in some cases joint replacement is needed. Thus, when certain cartilage damage is detected in a knee joint, the damage must be appropriately treated. Currently, cartilage damage is reliably detected by means of an arthroscope. However, arthroscopy is a cumbersome technique requiring high technical skill. Under such circumstances, there is demand for means for assessing cartilage damage at high sensitivity and in a simple manner.

In one specific embodiment of the disease detection of the present invention (e.g., assessment of the cartilage damage on a knee joint), the cartilage damage can be confirmed when the keratan sulfate level of a test specimen (synovial fluid or a blood specimen) is higher than the keratan sulfate level of the normal specimen, or when the keratan sulfate level of the test specimen determined by one measurement (the second or subsequent measurement among a plurality of measurements with an interval or intervals) has increased as compared with the level determined in the preceding measurement.

In the cartilage damage assessing method, provided that the keratan sulfate level of the knee synovial fluid of a specimen-donor as determined in the preceding assessing procedure is unknown, e.g., in the first medical examination, knee joint cartilage damage of the specimen-donor can be assessed on the basis of the aforementioned "keratan sulfate level of the normal specimen." Also, in the following assessing procedure (the second or subsequent procedure) (e.g., at a follow-up examination), when cartilage is newly damaged or the degree of damage has increased, the keratan sulfate level of the knee synovial fluid in the following determination tends to increase, as compared with the keratan sulfate level in the preceding determination. Thus, according to the present invention, the cartilage damage of a knee joint can be reliably detected.

As described above, according to the disease detection method of the present invention, osteoarthritis of the knee can be accurately detected. Particularly, there can be detected knee osteoarthritis which cannot be detected by an X-ray examination or which is difficult to detect by an X-ray examination (e.g., osteoarthritis in an early stage). This is a remarkable effect of the present invention which has never been reported. In addition, according to the disease detection method of the present invention, traumatic arthropathy can be reliably detected.

As described above, the present invention also provides a detection kit for carrying out the disease detection method of the present invention.

Similar to the case of the aforementioned detection method of the present invention, examples of the anti-keratan sulfate antibody employed in the disease detection method or kit of the present invention include EFG-11, BCD-4, BCD-7, BC-261, BC-703, MK-172, and MK-202.

More preferred embodiments of the specific combination of the solid-phased anti-keratan sulfate antibody and the labeled anti-keratan sulfate antibody are the same as described above. Particularly in the case of detecting osteoarthritis or traumatic arthropathy of a human subject, in a most preferred embodiment, EFG-11 or BCD-7 is employed as a solid-phased anti-keratan sulfate antibody, and EFG-11 or BCD-7 is employed as a labeled anti-keratan sulfate antibody, or BCD-4 or MK-172 is employed as a solid-phased anti-keratan sulfate antibody, and BCD-4 or MK-172 is employed as a labeled anti-keratan sulfate antibody, since disease detection can be performed at considerably high efficiency, as shown in the Examples hereinbelow. Specific examples of the combination are the following 1) to 6).

1) solid-phased anti-keratan sulfate antibody: BCD-7, labeled anti-keratan sulfate antibody: BCD-7
2) solid-phased anti-keratan sulfate antibody: BCD-7, labeled anti-keratan sulfate antibody: EFG-11
3) solid-phased anti-keratan sulfate antibody: EFG-11, labeled anti-keratan sulfate antibody: BCD-7
4) solid-phased anti-keratan sulfate antibody: EFG-11, labeled anti-keratan sulfate antibody: EFG-11
5) solid-phased anti-keratan sulfate antibody: BCD-4, labeled anti-keratan sulfate antibody: MK-172
6) solid-phased anti-keratan sulfate antibody: MK-172, labeled anti-keratan sulfate antibody: BCD-4

[Remedy Effect Assessing Method]

The determination method of the present invention enables highly sensitive determination of keratan sulfate in a specimen. Thus, the method can be applied to assessment of the effect of a remedy administered for the treatment of a joint disease and to selection of a candidate substance for the remedy for a joint disease through screening.

A described above, the remedy effect assessing method of the present invention is a method for assessing the therapeutic effect of a remedy for a joint disease or a candidate substance therefor, which method is characterized by comprising the following steps:

1) a step of determining the keratan sulfate level of a test specimen through the determination method of the present invention before and after administration of the joint disease remedy or a candidate substance therefor (remedy or the like) to a subject (first step);

2) a step of comparing the keratan sulfate level of the test specimen before administration of the remedy or the like with the keratan sulfate level of the test specimen after administration thereof, the levels having been determined in 1) (second step); and 3) a step of detecting, on the basis of the comparison in 2), the extent of a change in keratan sulfate level, said change being from the keratan sulfate level before administration of the remedy or the like to that level after administration thereof, to see whether there is any tendency toward a normal level, to thereby assess the effect of the joint disease remedy or the like based on the extent of the change as an index (third step).

When the remedy effect is assessed in the first step, the specimen-donor is a human or a non-human animal to be treated with the remedy. In the drug screening, the specimen-donor is generally a laboratory animal in which a joint disease has been induced, and the animal which is preferably employed may be a small animal such as the aforementioned guinea pig, rat, or mouse. The specimen may be selected from among synovial fluid, a blood specimen (serum, plasma, and whole blood), a urine specimen, etc., depending on the purpose.

The same anti-keratan sulfate antibodies as described in relation to the disease detection method of the present invention may be employed.

In these steps, the keratan sulfate level of the test specimen before administration of the remedy or the like is compared with the keratan sulfate level of the test specimen after administration thereof, the levels having been determined through the determination method of the present invention, whereby the effect of the remedy or the like or the therapeutic effect of the test substance on the target joint disease can be investigated.

In other words, in a clinical setting, when the keratan sulfate level determined through the determination method of the present invention after administration of the joint disease remedy has been changed toward the keratan sulfate level of a healthy subject; i.e., toward a normal level, the effect of the remedy on the joint disease to be treated is actually or potentially confirmed. Thus, according to the present invention, the effect of administration of the joint disease remedy can be assessed. As used herein, the term "actual effect" refers to a clinical effect being confirmed, and the term "potential effect" refers to biochemical test data having been changed toward a normal level, although no clinical effect is currently observed.

In addition, when the keratan sulfate level of a laboratory animal in which a joint disease has been induced has changed toward a normal level after administration of the test substance, the test substance is evaluated to have a therapeutic action on the joint disease. Thus, according to the present invention, screening of a joint disease remedy can be performed.

The present invention also provides an assessing kit for carrying out the aforementioned remedy effect assessing method of the present invention.

EXAMPLES

The present invention will next be described in detail by way of examples, which should not be construed as limiting the invention thereto.

The abbreviations employed in the Examples are as follows.
GAG: glycosaminoglycan
KS: keratan sulfate
KSPG: keratan sulfate proteoglycan
HA: hyaluronic acid
Ch: chondroitin
CS-A or CSA: chondroitin sulfate A
CS-A(S) or CSA(S): shark-derived chondroitin sulfate A
CS-A(W) or CSA(W): whale-derived chondroitin sulfate A
CS-B or CSB: chondroitin sulfate B
CS-C or CSC: chondroitin sulfate C
CS-D or CSD: chondroitin sulfate D
CS-E or CSE: chondroitin sulfate E
EDC: 1-methyl-3-(3-dimethylaminopropyl)carbodiimide
HEP: heparin
HRP: horseradish peroxidase
HS: heparan sulfate
Tris: 2-amino-2-hydroxymethyl-1,3-propanediol
PBS: phosphate buffered saline
EDC: N-ethyl-N'-(3-dimethylaminopropyl)carbodimide
BSA: bovine serum albumin
TMB: 3,3',5,5'-tetramethylbenzidine
Bi: biotin
MES: 2-morpholinoethanesulfonic acid
ELISA: enzyme-linked immunosorbent assay
competitive ELISA: enzyme-linked immunosorbent assay based on competitive technique Referential Example 1

Preparation of Biotin-Labeled GAG (Hereinafter Referred to as "Bi-GAG")

Each of GAGs (HS, HA, HEP, Ch, CS-A(S), CS-A(W), CS-B, CS-C, CS-D, CS-E, and KS) was dissolved in 0.1M MES buffer (pH: 5.5), to thereby prepare 10-mg/mL GAG solution. To each GAG solution (1 mL), 20 mM solution (25 µL) of biotin-LC-hydrazide (product of Pierce Biotechnology) dissolved in dimethylsulfoxide (product of Wako Pure Chemical Industries, Ltd.) was added. Subsequently, 100-mg/mL EDC (product of Pierce Biotechnology) solution (12.5 µL) prepared with 0.1M MES buffer (pH: 5.5) was added thereto. The mixture was sufficiently mixed, and then allowed to react under stirring at ambient temperature (15° C. to 25° C.) for 16 to 24 hours.

After completion of the reaction, the reaction products were dialyzed by use of a dialysis membrane (cutoff molecular weight: 10,000 or less) and phosphate buffered saline (pH: 7.2 to 7.5, containing no divalent ions such as calcium ion: hereinafter may be referred to as "PBS(−)") serving as a dialysis solution, to thereby sufficiently remove free biotin. After completion of dialysis, the concentration of Bi-GAG was adjusted to 5 mg/mL, followed by freeze preservation.

Through the above procedure, a variety of Bi-GAGs (Bi-HS, Bi-HA, Bi-HEP, Bi-Ch, Bi-CSA(S), Bi-CSA(W), Bi-CSB, Bi-CSC, Bi-CSD, Bi-CSE, and Bi-KS) were produced.

Notably, HEP employed was a product of SPL, and other GAGs employed were obtained from Seikagaku Corporation.

Referential Example 2

Production of Streptavidin-Immobilized Plate

Streptavidin (product of Vector Laboratories Inc.) was diluted with PBS(−) to a concentration of 20 µg/mL, and this streptavidin solution was added to a MaxiSorp (registered trademark) 96-well microplate (product of Nalge Nunc International K.K.) at 50 µL/well. The plate was stored at 4° C. for 14 to 18 hours to coat the plate uniformly. The plate was washed twice with PBS(−), and then phosphate buffer (PBS (−) containing no sodium chloride or no potassium chloride, pH: 7.2 to 7.5: hereinafter referred to as "PB") containing Applie Duo (final dilution factor: 5 fold, registered trademark, product of Seikagaku Corporation) serving as a blocking agent for blocking a part of the well uncoated with streptavidin and 0.05% ProClin (registered trademark) 950 (product of SUPELCO) serving as an antiseptic was added thereto. The plate was allowed to stand at ambient temperature for two hours. Thereafter, the blocking solution was sufficiently removed, and the plate was dried at 37° C. for two hours, to thereby yield a streptavidin-immobilized plate of interest. The plate was packed in an aluminum-laminated bag together with a desiccant, and stored in a refrigerator.

Referential Example 3

Production of Bi-GAG-Immobilized Plate

Bi-GAG prepared in Referential Example 1 was dissolved in TBS (50 mM Tris-HCl, pH: 7.3 to 7.8) containing Applie Duo (registered trademark) (final dilution factor: 20 fold, product of Seikagaku Corporation) serving as an additive, 0.05% Tween (registered trademark) 20 (0.05% polyoxyethylene (20) sorbitan monolaurate, ICI, a product corresponding to Tween 20, available from Wako Pure Chemical Industries, Ltd.), and 0.05% ProClin (registered trademark) 950 serving as an antiseptic (hereinafter referred to as "reaction mixture A"), to thereby yield a 1 µg/mL Bi-GAG solution. The streptavidin-immobilized plate prepared in Referential Example 2 was washed four times with 300 µL of 50 mM Tris-HCl (pH: 7.3 to 7.8) containing 0.05% Tween 20 and 0.05% Proclin (registered trademark) 950 serving as an antiseptic (T-TBS, hereinafter referred to as "washing liquid"). Then, the Bi-GAG solution was added at 100 µL/well, and the plate was allowed to stand at ambient temperature for 30 minutes, to thereby immobilize Bi-GAG to the immobilized streptavidin (hereinafter referred to as "Bi-GAG-immobilized plate). When each immobilized GAG species is indicated, "GAG in "Bi-GAG" is substituted by each abbreviation of the specific GAG species.

Referential Example 4

Purification of Antibodies

An ascites containing each KS antibody shown in Table 4 (available from Rush University Medical Center) was subjected to affinity chromatography employing protein A, to thereby purify the antibody in a routine manner.

Referential Example 5

Production of Peroxidase-Labeled Antibodies

Eight purified antibodies obtained in Referential Example 4 (each 0.2 mg) was labeled with peroxidase by means of Quick labeler Pro-PO $NH_2$ (available from Seikagaku Corporation) according to an attached manual, to thereby prepare corresponding peroxidase-labeled antibodies.

Referential Example 6

Production of Anti-KS Antibody-Immobilized Plate

The procedure of Referential Example 2 was repeated, except that each of the anti-KS antibodies purified in Referential Example 4 was used instead of streptavidin, to thereby produce each anti-KS antibody-immobilized plate.

Referential Example 7

Collection of Specimens of Joint Disease Patients

With the approval of the ethics committee of the relevant medical center and informed consent of patients, blood was collected from 29 knee osteoarthritis (OA) patients; 17 traumatic knee arthropathy (TA) patients who had visited the doctor for trauma in a knee joint caused by sports activity, accident, etc. and had degeneration or damage of the articular cartilage as observed through arthroscopy or under direct vision during the course of surgery; and 18 healthy subjects. Blood was collected by means of a commercial blood collection tube for serum separation. After separation, the separated serum was stored at −20° C.

Example 1

Reactivity of Anti-KS Antibody with KS-I and KS-II

The reactivity of each anti-KS antibody with KS-I and that with KS-II were evaluated through so-called competitive ELISA in which binding of the anti-KS antibody to biotin-labeled KS-I (hereinafter referred to as "Bi-KS") is inhibited by KS-I or KS-II.

The Bi-KS-immobilized plate produced through the procedure of Referential Example 3 was washed four times with a washing liquid. To each well, a KS-I solution or a KS-II solution (concentration: 100 to 0 ng/mL, 5-fold dilution series) (100 μL) was added, and a solution of each anti-KS antibody (5D4: purified antibody diluted solution, other antibodies: ascites diluted solution, dilution factor and concentration of tested anti-KS antibody shown in Table 3) was added to the wells at 100 μL/well. The plate was then allowed to stand at ambient temperature for 60 minutes to thereby carry out antigen-antibody reaction. A well to which no Bi-KS was added was employed as a blank. After completion of reaction, the plate was washed four times with the washing liquid, and a secondary antibody solution (HRP-labeled goat anti-mouse immunoglobulin antibody (product of Dako), 2.000-fold diluted with the reaction mixture) was added to each well at 100 μL/well. The plate was allowed to stand at ambient temperature for 60 minutes to thereby carry out antigen-antibody reaction. After completion of reaction, the plate was washed four times with the washing liquid, and TMB solution (trade name: TMB 1 Component HRP Microwell Substrate, product of BioFX) (100 μL/well) serving as a substrate of peroxidase was added. The plate was allowed to react at ambient temperature for 30 minutes, to thereby develop color. Through addition of a reaction-terminating liquid (product of BioFX) (100 μL/well) to the plate, the reaction was terminated. Subsequently, an absorbance at 450 nm (with respect to 630 nm) increased by decomposition of TMB was measured by means of a well reader SK-603 (registered trademark, available from Seikagaku Corporation). The reactivity of each antibody was evaluated as IC50, which was calculated from the percent inhibition when an inhibiting substance was employed. From the thus-obtained reactivity, reactivity of KS-I and that of KS-II were assessed.

As an inhibiting substance, KS(BC) (available from Seikagaku Corporation) was used with respect to KS-I, and KPS-1 (product of Seikagaku Corporation) was used with respect to KS-II. The test concentration was adjusted to 100 to 0 ng/mL (5-fold dilution series).

In order to assess the difference between reactivity of each KS antibody with KS-I and that with KS-II, the ratio of IC50 of KS-I to IC50 of KS-II ($IC50^{KS-I/KS-II}$) was calculated for each KS antibody. Notably, when $IC50^{KS-I/KS-II}$ is close to 1, the difference between reactivity with KS-I and that with KS-II is smaller; i.e., the reactivity of the anti-keratan sulfate antibody with KS does not greatly depend on the sulfate content.

Percent inhibition was obtained by subtracting the blank absorbance from the absorbance of each well, and dividing the residual absorbance difference by the absorbance difference of a well containing only Bi-KS (maximum absorbance difference), wherein the residual absorbance difference is obtained by subtracting the absorbance difference at each inhibiting substance concentration from the maximum absorbance difference.

TABLE 3

Isotype and test dilution factor/test concentration of anti-KS antibodies

| Anti-KS antibody | Isotype | Test Dilution factor/ Test concentration |
|---|---|---|
| BCD-4 | IgG1 | ×100000 |
| BCD-7 | IgG1 | ×20000 |
| BC-261 | IgG1 | ×20000 |
| BC-703 | IgG3 | ×10000 |
| MK-172 | IgG3 | ×50000 |
| MK-202 | IgG1 | ×100000 |
| EFG-11 | IgG2b | ×500000 |
| 5D4 | IgG1 | 0.3 μg/mL |

Table 4 and FIG. 1 show the results.

TABLE 4

IC50 of anti-KS antibody with respect to KS-I and KS-II

| Anti-KS antibody | IC50 (ng/mL) | | $IC50^{KS-I/KS-II}$ |
|---|---|---|---|
| | KS(BC) | KPS-1 | |
| BCD-4 | 5.82 | 3.62 | 1.6 |
| BCD-7 | 4.09 | 1.17 | 3.5 |
| BC-261 | 1.59 | 1.46 | 1.1 |
| BC-703 | 2.56 | 0.67 | 3.8 |
| MK-172 | 6.79 | 7.88 | 0.9 |
| MK-202 | 7.62 | 19.87 | 0.4 |
| EFG-11 | 0.63 | 0.20 | 3.2 |
| 5D4 | 14.47 | 1.40 | 10.4 |

5D4 exhibited IC50 to KS-I of 14.47 ng/mL and that to KS-II of 1.40 ng/mL. The other seven KS antibodies exhibited IC50 to KS-I lower than that of 5D4, 14.47 ng/mL. Therefore, these seven KS antibodies were found to have higher reactivity with KS-I than did 5D4. The IC50 to KS-II of BCD-7, BC-703, and EFG-11 were lower than that of 5D4. Thus, these three antibodies exhibited reactivity with KPS-1 higher than that of 5D4.

5D4 exhibited an $IC50^{KS-I/KS-II}$ of 10.4, indicating that the reactivity with KS-I was about 1/10 of that with KS-II. The other seven anti-KS antibodies exhibited an $IC50^{KS-I/KS-II}$ which is lower than that of 5D4. Therefore, as compared with 5D4, these seven antibodies were found to have a lower sulfate content dependency in antigen-antibody reaction.

Example 2

Sandwich ELISA

Sandwich ELISA employing 5D4 was performed by means of a commercial keratan sulfate assay kit (available from Seikagaku Corporation) in accordance with a manual attached thereto.

The assay according to the determination method of the present invention was carried out in the following manner.

The anti-KS antibody-immobilized plate produced through the procedure of Referential Example 6 was employed as an anti-KS antibody-immobilized plate. The HRP-labeled anti-KS antibody produced through the procedure of Referential Example 5 was employed as an anti-KS antibody for detection. The following 12 combinations of the solid-phased antibody and the detection antibody were tested.
1) Solid-phase: BCD-4, Detection: BCD-4
2) Solid-phase: BCD-4, Detection: MK-172
3) Solid-phase: MK-172, Detection: MK-172
4) Solid-phase: MK-172, Detection: BCD-4
5) Solid-phase: EFG-11, Detection: EFG-11
6) Solid-phase: BCD-7, Detection: BCD-7
7) Solid-phase: EFG-11, Detection: BCD-7
8) Solid-phase: MK-202, Detection: MK-202
9) Solid-phase: BCD-7, Detection: EFG-11
10) Solid-phase: BC-261, Detection: BC-261
11) Solid-phase: BC-703, Detection: BC-703

The reaction mixture A employed in Referential Example 3 (100 μL/well) was added to each well of each anti-KS antibody-immobilized plate. Subsequently, a test solution containing keratan sulfate shown in Table 5 or a blank solution (20 μL/well) was added to the plate. The plate was gently stirred and allowed to stand at 15 to 25° C. for one hour (first reaction). After completion of the first reaction, the reaction mixture was removed, and the plate was washed four times with a washing liquid (300 μL/well). After washing, a HRP-labeled anti-KS antibody (800-fold diluted) (100 μL/well) was added to each well, and the plate was allowed to stand at 15 to 25° C. for one hour (second reaction). After completion of the second reaction, the plate was washed four times with the washing liquid in the same manner. After washing, a TMB solution (product of BioFX) (100 μL/well) serving as a substrate of HRP was added to the plate, and the plate was allowed to statically react at ambient temperature for 30 minutes under light shielding conditions, to thereby develop color (coloring reaction). After color development, 1N HCl (100 μL) was added to the plate so as to terminate the reaction. Subsequently, an absorbance of the color-developed liquid at 450 nm (with respect to 630 nm) increased by decomposition of TMB was measured by means of a well reader SK-603 (registered trademark, available from Seikagaku Corporation). The results of the sandwich ELISA were evaluated on the basis of the difference in absorbance between each test solution and the blank solution.

Figure 2:
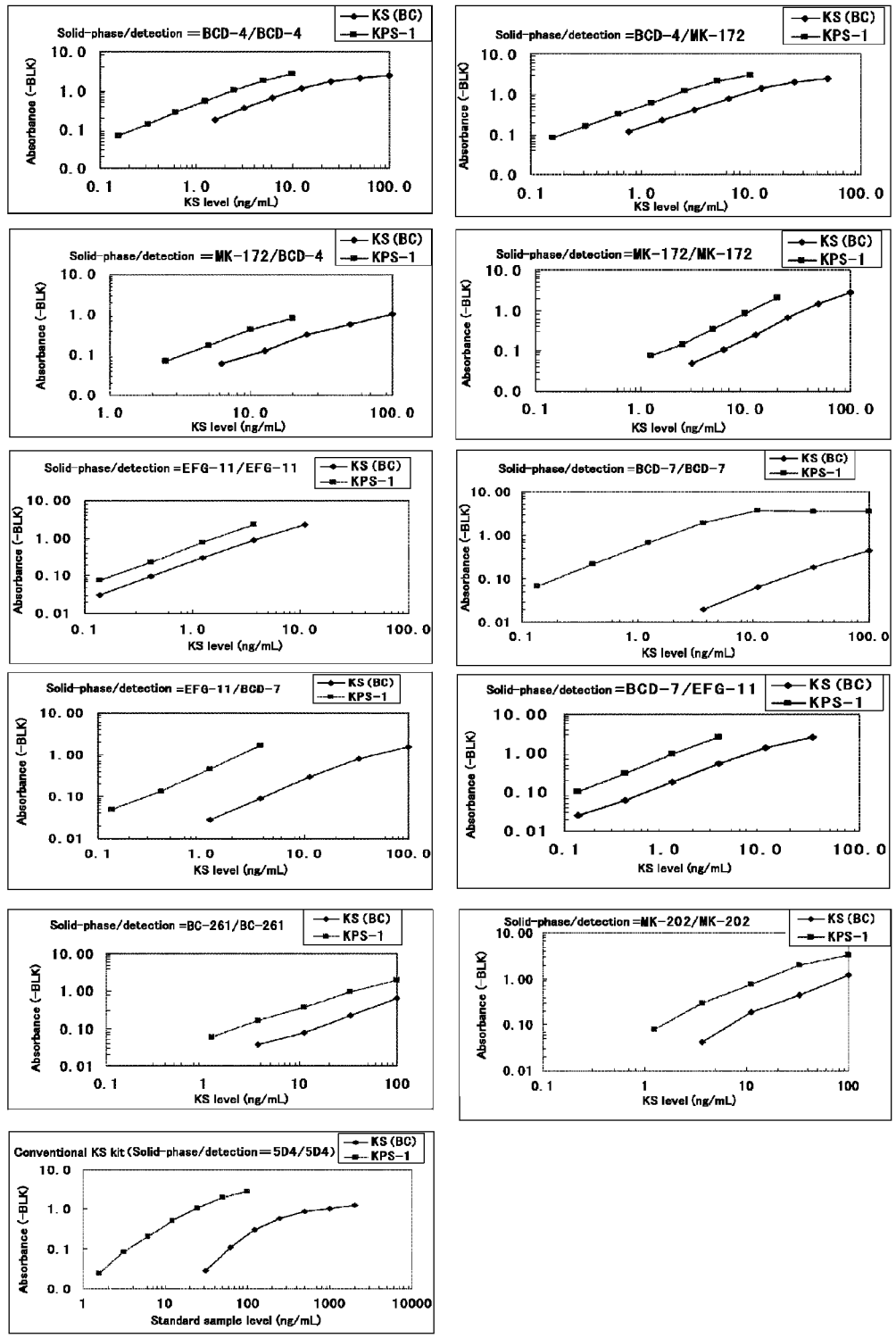
FIG. 2 shows reaction curves of keratan sulfate obtained through sandwich ELISA.

In the concentration dependency test in terms of KS(BC) (KS-I) and KPS-1 (KS-II), antibody combinations shown in Table 5 were employed, and KS(BC) and KPS-1 were tested at concentrations shown in Table 5. The obtained reaction curves were compared. FIG. 2 shows the results.

TABLE 5

Test Concentrations of KSs

| Solid phase | Detection | Test concentration (ng/mL, twice- or thrice-diluted series) | |
|---|---|---|---|
| | | KS-I (KS(BC)) | KS-II (KPS-1) |
| 5D4 | 5D4 | 2000-31.25 | 100-1.5625 |
| BCD-4 | BCD-4 | 100-1.5625 | 10-0.15625 |
| BCD-4 | MK-172 | 50-0.78125 | 10-0.15625 |
| MK-172 | BCD-4 | 100-6.25 | 20-1.25 |
| MK-172 | MK-172 | 100-3.125 | 20-0.625 |
| EFG-11 | EFG-11 | 100-0.14 | |
| BCD-7 | BCD-7 | 100-0.14 | |
| EFG-11 | BCD-7 | 100-0.14 | |
| EFG-11 | BCD-7 | 100-0.14 | |
| BC-261 | BC-261 | 100-0.14 | |
| MK-202 | MK-202 | 100-0.14 | |

In the assay system employing 5D4, the KS(BC) concentration and the KPS-1 concentration which provide an absorbance of 1.0 were 921.7 ng/mL and 25.5 ng/mL, respectively. The KPS-1 concentration in any antibody combination employed in the determination method of the present invention is lower than that obtained through a conventional 5D4 method, indicating that the sensitivity of the method of the present invention is higher than that provided by the conventional 5D4 method. Also, the KS(BC) concentration obtained through the determination method of the present invention is lower than that obtained through the conventional 5D4 method, in nine antibody combinations other than solid-phase: BCD-7/detection: BCD-7, indicating that the sensitivity of the method of the present invention is higher than that provided by the conventional 5D4 method. In the above expression of the antibody combinations, "solid-phased anti-KS antibody" is placed on the left side of "/", and "detection anti-KS antibody" on the right side of "/." This convention may be used hereinafter, without placing the word "antibody." Differing from the nine antibody combinations, the reactivity in the case of solid-phase: BCD-7/detection: BCD-7 is thought to be exceptionally almost equivalent to or slightly higher than that obtained through the conventional 5D4 method.

Separately, in order to evaluate KS detection performance in various antibody combinations, the KS(BC) concentration and the KPS-1 concentration which provide an absorbance difference of 1.0 calculated from the corresponding concentration dependency curve (represented by KS(BC) (1.0) and KPS-1 (1.0), respectively), as well as the relative detection performance (KS(BC) (1.0)/KPS-1 (1.0), hereinafter may be referred to as "detection performance ratio$^{KS\text{-}I/KS\text{-}II}$") were also calculated. Table 6 shows the results.

TABLE 6

Reactivity with KS in sandwich ELISA
(concentration providing absorbance difference 1.0)

| Solid-phased antibody | Detection antibody | KSBC (1.0) | KPS-1 (1.0) | KSBC (1.0)/KPS-1 (1.0) |
|---|---|---|---|---|
| 5D4 | 5D4 | 921.7 | 25.5 | 36.1 |
| BCD-4 | BCD-4 | 11.6 | 2.6 | 4.5 |
| BCD-4 | MK-172 | 9.1 | 2.1 | 4.3 |
| MK-172 | BCD-4 | 86.1 | 23.2 | 3.7 |
| MK-172 | MK-172 | 36.8 | 11.3 | 3.3 |
| EFG-11 | EFG-11 | 4.3 | 1.6 | 2.7 |
| BCD-7 | BCD-7 | >100 | 1.8 | >55.6 |
| EFG-11 | BCD-7 | 8.1 | 1.4 | 6.0 |
| BCD-7 | EFG-11 | 49.1 | 2.4 | 20.2 |
| BC-261 | BC-261 | 80.0 | 14.3 | 5.6 |
| MK-202 | MK-202 | 81.2 (ng/mL) | 15.1 (ng/mL) | 5.4 |

In the assay system employing 5D4, the detection performance ratio$^{KS\text{-}I/KS\text{-}II}$ was found to be 36.1, indicating that the KS(BC) detection performance is about 1/36 of the KPS-1 detection performance. Among the tested antibody combinations, nine combinations other than solid-phase: BCD-7/detection: BCD-7, showed detection performance ratios$^{KS\text{-}I/KS\text{-}II}$ of 2.7 to 20.2, which is lower than that obtained through the conventional 5D4 method. Thus, as compared with the conventional 5D4 method, the determination method of the invention can detect KS with lower dependency on sulfate content. Meanwhile, although the IC50$^{KS(BC)/KPS\text{-}1}$ was lower than that obtained through the conventional 5D4 method when BCD-7 was employed as a sole antibody, the combination of solid-phase: BCD-7/detection: BCD-7 among the tested combinations provided an exceptional detection performance ratio$^{KS\text{-}I/KS\text{-}II}$ of 55.6 or higher, which is thought to be higher than that obtained through the conventional 5D4 method.

The detection performance test was further performed with a variety of specimens shown in Table 7. The obtained performance was evaluated.

TABLE 7

Dilution factors of specimens

| Solid-phase | Detection | Human Serum | Rabbit Serum | Guinea pig Serum | Guinea pig Synovial fluid | Rat Serum | Rat Synovial fluid | Mouse Serum |
|---|---|---|---|---|---|---|---|---|
| 5D4 | 5D4 | X20 | X5 | X5 | X5 | X5 | X5 | X5 |
| BCD-4 | BCD-4 | X4800 | X120 | X600 | X120 | X30 | X30 | X6 |
| BCD-4 | MK-172 | | | | | | | |
| MK-172 | BCD-4 | | | | | | | |
| MK-172 | MK-172 | | | | | | | |
| EFG-11 | EFG-11 | — | | | — | | — | — |
| BCD-7 | BCD-7 | | | | | | | |
| EFG-11 | BCD-7 | | | | | | | |
| BCD-7 | EFG-11 | | | | | | | |

(Dilution factor: final in assay, —: not tested)

Tables 8 and 9 show the results. The tested samples in Table 8 are different from those in Table 9.

TABLE 8

Detection performance of samples - 1

| Solid-phase | Detection | | Human Serum | Rabbit Serum | Guinea Pig Serum | Guinea Pig Synovial fluid | Rat Serum | Rat Synovial fluid | Mouse Serum |
|---|---|---|---|---|---|---|---|---|---|
| 5D4 | 5D4 | Dilution factor | x10 | X5 | x5 | x5 | x5 | x5 | x5 |
| | | Abs. difference | 0.913 | 0.136 | n.d. | 0.100 | n.d. | n.d. | n.d. |
| BCD-4 | BCD-4 | Dilution factor | X4800 | x120 | X600 | x120 | x30 | x30 | x6 |
| | | Abs. difference | 1.054 | — | 0.519 | 0.535 | 0.680 | 0.262 | — |
| BCD-4 | MK-172 | | 1.372 | 0.498 | 0.859 | 0.750 | 1.261 | 0.356 | 0.430 |

TABLE 8-continued

Detection performance of samples - 1

| Solid-phase | Detection | Human Serum | Rabbit Serum | Serum | Guinea Pig Synovial fluid | Serum | Rat Synovial fluid | Mouse Serum |
|---|---|---|---|---|---|---|---|---|
| MK-172 | BCD-4 | — | — | 0.063 | 0.030 | 0.113 | 0.014 | — |
| MK-172 | MK-172 | 0.200 | — | 0.241 | 0.113 | 0.931 | 0.052 | — |

(Dilution factor: final in assay, —: not tested)

In the assay system employing 5D4 shown in Table 8, the human serum sample (10-fold diluted) exhibited an absorbance difference of 0.913. The four assay systems employing a combination of BCD-4 and MK-172 attained a sufficient absorbance difference at a dilution factor of 4,800 (except the case of the combination of solid-phase: MK-172/detection: BCD-4 not tested). Thus, the assay system of the invention can detect KS at higher sensitivity as compared with the conventional system employing 5D4.

Among the other samples derived from rabbit, guinea pig, rat, and mouse, the 5D4 system detected KS only in the rabbit serum sample and the guinea pig synovial fluid sample, but the absorbance difference values were as low as 0.136 and 0.1, respectively. The 5D4 system could not detect KS in the other samples.

Among the assay systems employing the four antibody combinations shown in Table 8, the case of solid-phase: MK-172/detection: BCD-4 exhibited lower detection performance as compared with the remaining three systems. The three systems other than the system employing solid-phase: MK-172/detection: BCD-4 detected KS in all specimens at higher sensitivity as compared with the 5D4 system. Particularly, the combination of solid-phase: BCD-4/detection: MK-172 was found to provide a high KS detection sensitivity.

TABLE 9

Detection performance of samples -2

| Solid-phase | Detection | | Rabbit Serum | Guinea pig Serum | Rat Serum | Mouse Serum |
|---|---|---|---|---|---|---|
| | | Dilution factor | X5 | x5 | x5 | x5 |
| 5D4 | 5D4 | Abs. difference | 0.150 | 0.230 | n.d. | n.d. |
| | | Dilution factor | x120 | X600 | in parenthesis | x6 |
| EFG-11 | EFG-11 | Abs. difference | 2.802 | 0.556 | 0.528(X30) | n.d. |
| BCD-7 | BCD-7 | | 0.257 | 0.152 | 0.194(X6) | n.d. |
| EFG-11 | BCD-7 | | 0.468 | 0.239 | 0.186(X30) | n.d. |
| BCD-7 | EFG-11 | | 1.153 | 0.606 | 0.485(X30) | n.d. |

(Dilution factor: final in assay)

In the test shown in Table 9, through the 5D4 method, KS was detected in the rabbit serum sample and the guinea pig serum sample with absorbance differences as low as 0.150 and 0.230, respectively. Similar to Table 8, KS could not be detected in the rat serum sample and the mouse serum sample.

The assay systems employing all four antibody combinations shown in Table 9 could sufficiently detect KS in the rabbit serum samples and the guinea pig serum samples and KS in the rat serum samples, which has not been attained through the conventional 5D4 method. Among the four antibody combinations, the systems employing solid-phase: BCD-7/detection: BCD-7 and solid-phase: EFG-11/detection: BCD-7 exhibited relatively lower detection performance as compared with the two other combinations. Thus, similar to the 5D4 method, the assay systems employing the four antibody combinations shown in Table 9 could not detect KS in the mouse serum samples. However, the four antibody combinations were found to provide a higher KS detection sensitivity, as compared with the 5D4 method.

As is clear from Tables 8 and 9, the assay system of the present invention was found to enable detection of KS in various samples at higher sensitivity as compared with the conventional 5D4 method, and also enable detection of a micro-amount of KS, which has not been detected through the conventional technique. In particular, the combination of solid-phase: BCD-4/detection: MK-172 enabled detection of a very small amount of KS in mouse serum samples.

Example 3

The serum KS levels of serum specimens in which protein had been digested with pronase and specimens which had undergone no pronase treatment were determined by means of a BCD-4/MK172 assay system and an EFG11/EFG11 assay system. The assay results were compared with the serum KS levels determined through HPLC. The assayed specimens were a part of the samples collected in Referential Example 7; i.e., serum samples obtained from 15 healthy subjects and 20 OA patients. Each pronase-treated specimen was prepared by adding purified water (180 μL) and 2.0% Actinase E solution (product of Kaken Pharmaceutical Co., Ltd.) to serum (20 μL), and subjecting the mixture to an enzyme treatment overnight at 55° C. The reaction mixture was diluted with purified water to a volume of 8 mL, and the diluted product was heated at 100° C. for 10 minutes, to thereby terminate the enzymatic reaction. This product was employed as a sample to be assayed. The pronase-non-treatment specimen was prepared by diluting serum with purified water. The same ELISA procedure as employed in Example 2 was performed.

Figure 3:
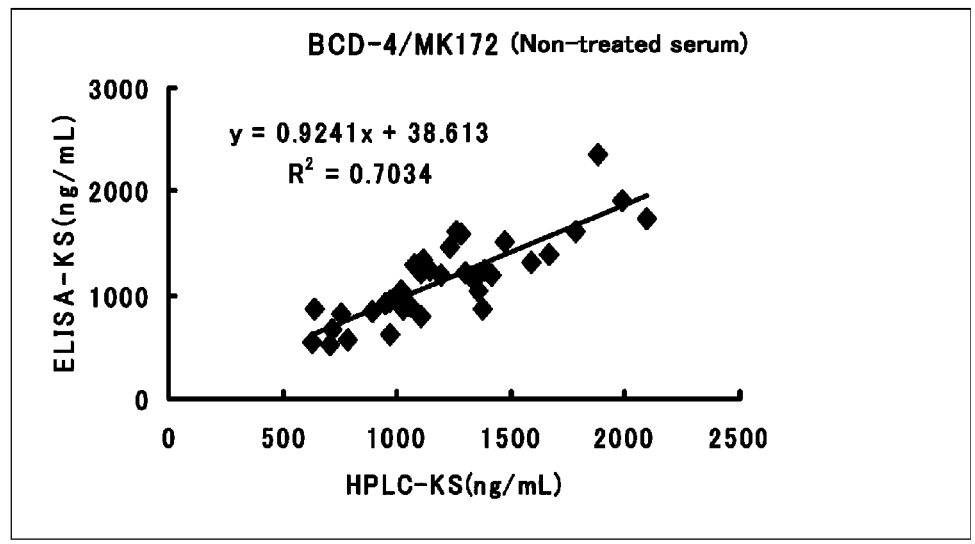
FIG. 3 shows correlation between keratan sulfate levels of serum samples determined through a BCD-4/MK172 assay system and those determined through HPLC, the samples being pronase-treated or pronase-non-treated.
Figure 3:
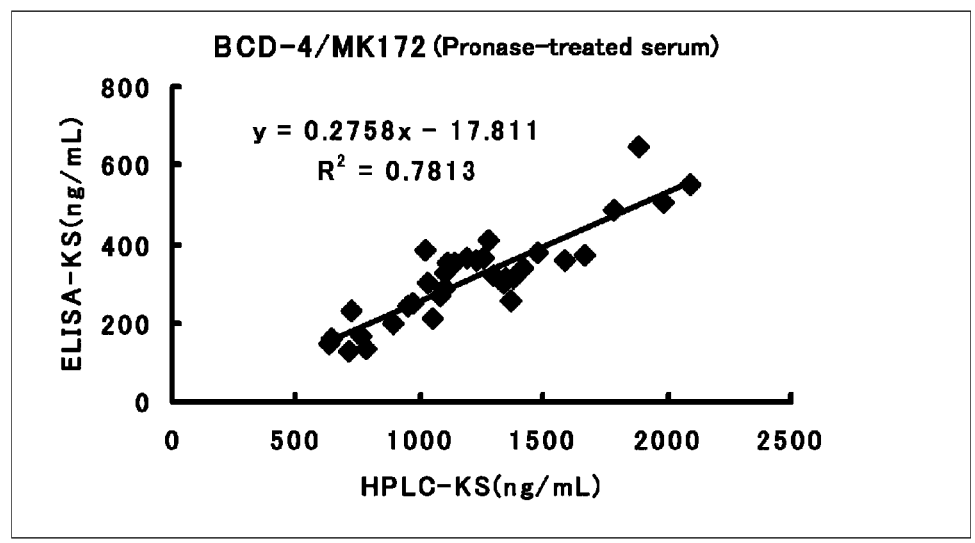

As shown in FIG. 3, the KS level of actinase-non-treated serum samples and pronase-treated serum samples determined by means of the BCD-4/MK172 assay system were found to be correlated to the KS levels determined through HPLC with correlation factors of $R^2$ of 0.7034 and 0.7813, respectively. Thus, the correlation was enhanced through the pronase treatment.

Figure 4:
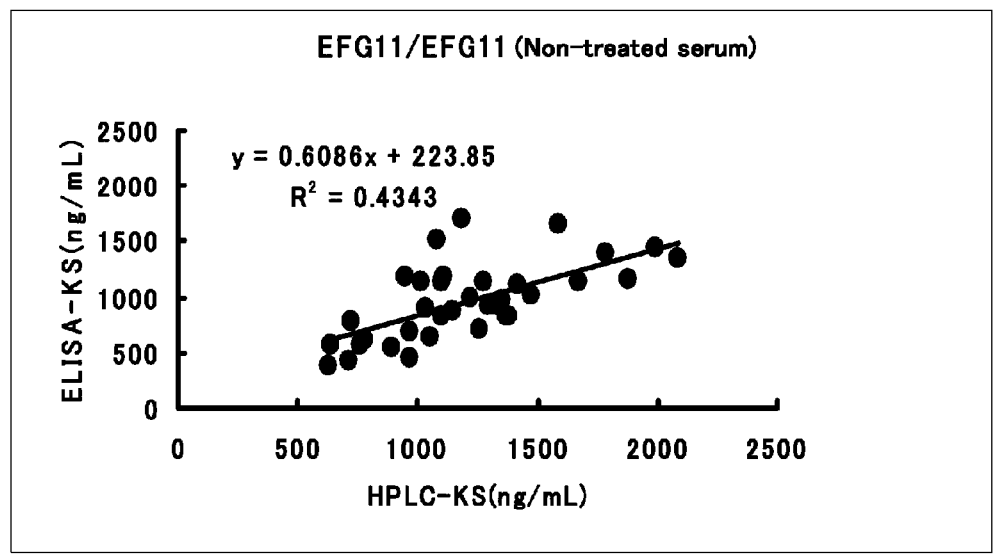
FIG. 4 shows correlation between keratan sulfate levels of serum samples determined through an EGF11/EGF11 assay system and those determined through HPLC, the samples being pronase-treated or pronase-non-treated.
Figure 4:
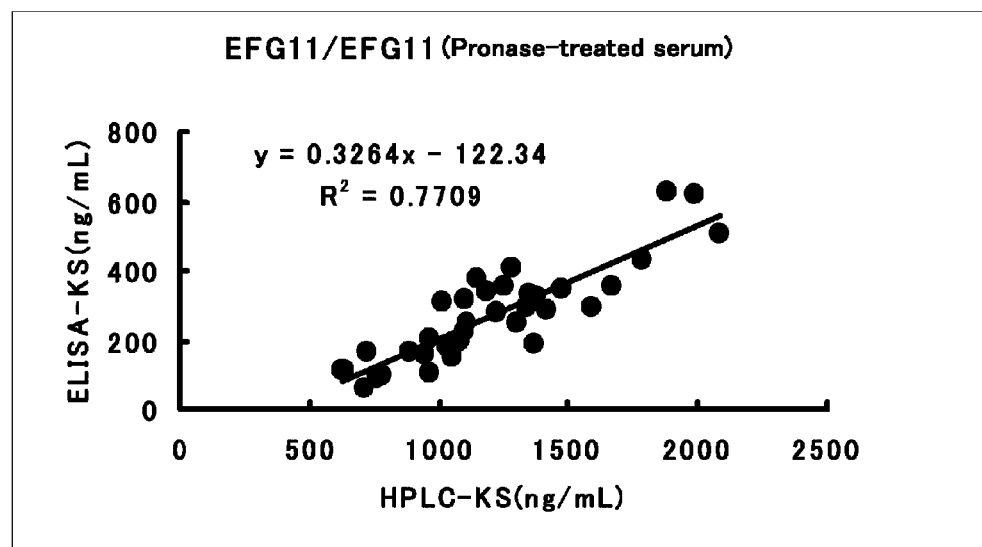

As shown in FIG. 4, through employment of the EFG11/EFG11 assay system, the correlation factor $R^2$ was enhanced from 0.4343 to 0.7709 through the pronase treatment.

Through the pronase treatment, correlation to the KS levels determined through HPLC was enhanced in both assay systems, leading to provision of more accurate measurements.

Example 4

Studies by Use of Meniscectomy Model Animal

In Example 4, 7-week-old male Wistar rats (SPF, Charles River Laboratories Japan, Inc.) were employed.

Test rats were anesthetized under the inhalation with isoflurane (Forane, product of Dainippon Pharma Co., Ltd.) (concentration: 2.0%, flow rate 3.0 L/min) charged into the small animal anesthetizer (TK-5, product of Biomachinery). Each rat was subjected to shaving around the left hindlimb knee joint, dissection (about 1 cm) of the inside of the joint, and cutting of the inside collateral ligament without damaging veins, to thereby expose the inside meniscus. Subsequently, the center of the meniscus was just laterally cut by means of a neuro-blade carving knife (K-5410, product of Feather). In addition, the peripheral ligament linking to the meniscus was cut, to thereby isolate a half of the meniscus. In the Sham group, only cutting of the inside collateral ligament was performed.

After completion of the operation, the cut portion was sutured. On day 28 after operation, the rats were euthanized through exsanguination under anesthesia with ether (product of Wako Pure Chemical Industries, Ltd.), and the left hindlimb knee joint tissue was collected from each rat. The joint cavity was washed with physiological saline and the synovial fluid (0.3 mL) was recovered, and the synovial fluid was centrifuged at 3,000 rpm for 10 minutes. The synovial fluid KS level (non-treated control group, Sham group, and meniscectomy group) on day 28 after operation was determined by means of a conventional KS assay kit (5D4 assay system) and through the KS assay system of the present invention. In the KS assay system of the present invention, a "solid-phase: BCD-4, detection: HRP-labeled MK-172" system was employed, and the assay was performed in a manner similar to that of Example 2.

Upon measurement, the samples were 5-fold diluted in the case of the conventional KS assay kit (5D4 assay system) and 60-fold diluted in the case of the KS assay system of the present invention. Separately, India ink was applied onto the tibia cartilage surface, and the surface was photographed by means of a digital camera (*istD, Pentax). Gross morphological changes were evaluated in terms of surface roughening with the following five grads (0: intact surface, 1: slight fibrillation, 2: severe fibrillation, 3: slight erosion, 4: severe erosion). In the case where osteophyte formation was observed at the joint peripheral portion, a point of "+1" was added to the corresponding rating.

(1) Joints Condition

Figure 5:
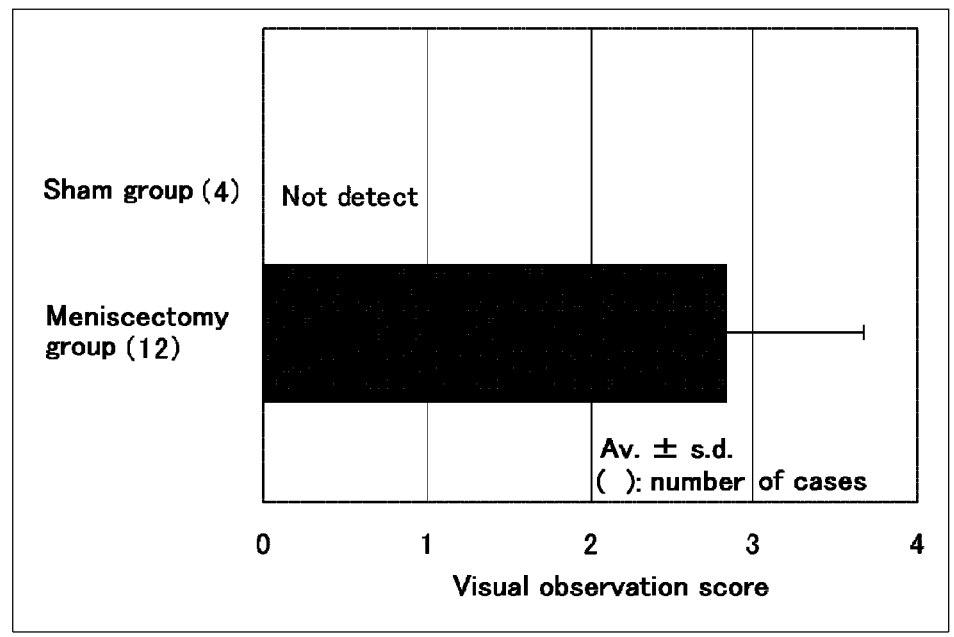
FIG. 5 shows visual observation scores of meniscectomy model rats.

FIG. 5 shows the gross morphological changes of cartilage surface of the rats belonging to the Sham group and the meniscectomy group on day 28 after operation. The average score of the meniscectomy group was significantly higher than that of the Sham group, indicating that the joint conditions were aggravated in the meniscectomy group.

(2) Synovial Fluid KS Levels

Figure 6:
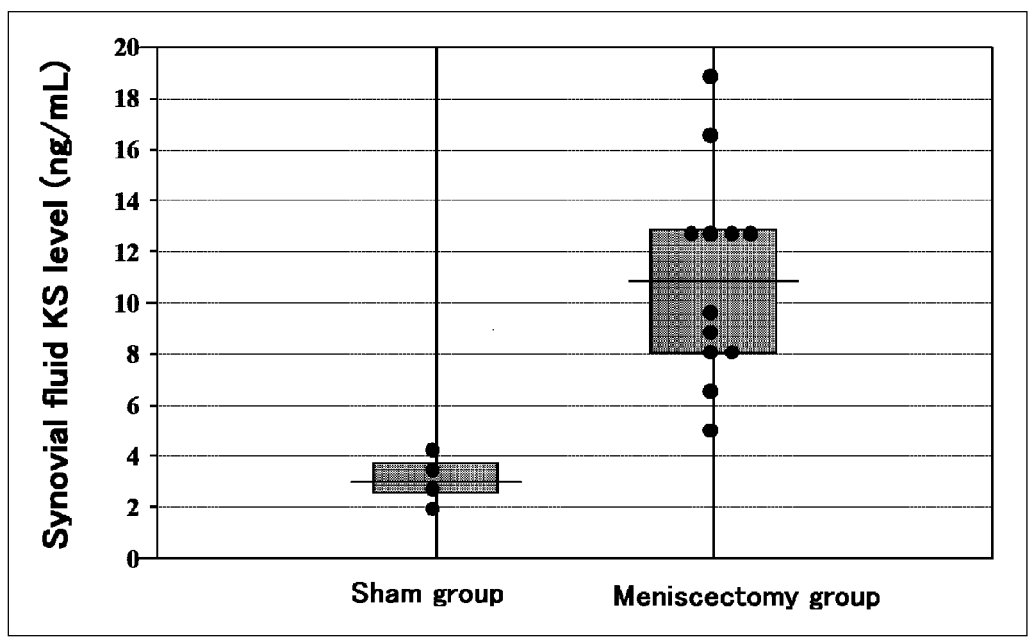
FIG. 6 shows keratan sulfate levels of synovial fluid samples obtained from meniscectomy model rats.

The synovial fluid KS levels of the meniscectomy model rat groups could not be detected by means of the conventional KS assay kit but could be detected by means of the assay system of the present invention. FIG. 6 shows only the results of the assay by means of the KS assay system of the present invention. As is clear from FIG. 6, the synovial fluid KS level of the meniscectomy group was significantly higher than that of the Sham group. Thus, the KS assay system of the present invention was found to enable detection of KS in samples whose KS cannot be detected by a conventional KS assay kit. Furthermore, on day 28 after operation the synovial fluid KS level of the meniscectomy model rats was found to have increased. In addition, the possibility that the determination of the synovial fluid KS level of the meniscectomy mode rats through the KS assay system of the present invention would lead to assessment of joint conditions was indicated.

As described above, the disease assessing method of the present invention may evaluate the damage of cartilage of the knee joint.

Example 5

Studies by Use of Adjuvant-Induced Arthritis (AIA) Model in Rats

In Example 5, 6-week-old male Lewis rats (SPF, Charles River Laboratories Japan, Inc.) were employed. The adjuvant was prepared by suspending heat-killed *Mycobacterium butyricum* (product of DIFCO) in liquid paraffin (product of Wako Pure Chemical Industries, Ltd.) at a concentration of 6 mg/mL. The adjuvant was subcutaneously administered to each of the rats in the right hind paw (0.3 mg/paw) without anesthesia. Fourteen days after administration, the rats were divided into 4 groups. To a non-treated normal control group, only liquid paraffin was administered to the rats in a similar manner. From the timing of the grouping, incadronate (Bisphonal (registered trademark) injection (10 mg), product of Astellas Pharma Inc.) was subcutaneously administered to the rats every day (once a day) at a dose of 1 mg/kg to the day before the day of sacrifice. To the rats of non-treated normal control group and the AIA control group, PBS was intravenously administered once a day to the day before the day of sacrifice. The edema volume of the left hind paw was measured by means of a volumetric apparatus (TK-101CMP, product of UNICOM). On day 35 after sensitization with the adjuvant, blood was collected (with heparin) from each rat through the abdominal vena cava under anesthesia with ether. Thereafter, the rats were euthanized through exsanguination. The collected blood was centrifuged at 3,000 rpm for 10 minutes. The plasma KS level (non-treated control group, AIA control group, and incadronate-administered group) was determined on day 35 after administration of the adjuvant, by means of a conventional KS assay kit (5D4 assay system) and through the KS assay system of the present invention. In the KS assay system of the present invention, a "solid-phase: BCD-4, detection: HRP-labeled MK-172" system was employed, and the assay was performed in a manner similar to that of Example 2. The dilution factor of the rat plasma was 5 fold (×5) in the case of the conventional KS assay kit and 120 fold (×120) in the case of the KS assay system of the present invention.

(1) Joint Conditions

Figure 7:
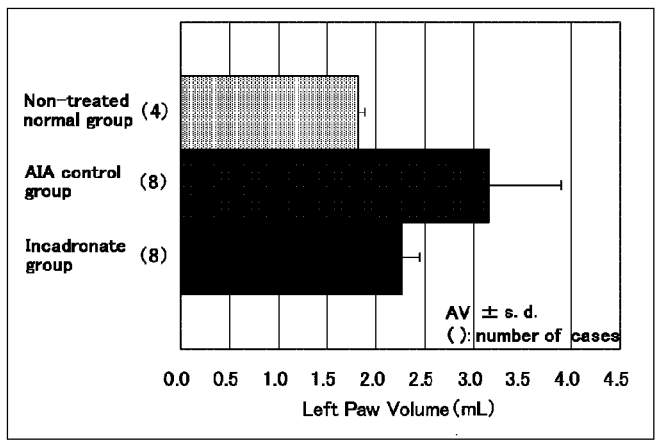
FIG. 7 shows keratan sulfate levels of synovial fluid samples of rats having an adjuvant-induced arthritis.

FIG. 7 shows the left paw volumes of the rats (non-treated normal control group, AIA control group, and incadronate (bisphosphonate preparation)-administered group (i.e., (adjuvant administration and incadronate administration)) on day 35 after administration of the adjuvant. As is clear from FIG. 7, the left paw volume of the AIA control group was significantly higher than that of the non-treated normal group, indicating that the joint conditions were aggravated. The left paw volume of the incadronate-administered group was reduced as compared with the AIA control group, indicating that the effect of the remedy (edema-ameliorating effect) was attained.

(2) Plasma KS Levels

Figure 8:
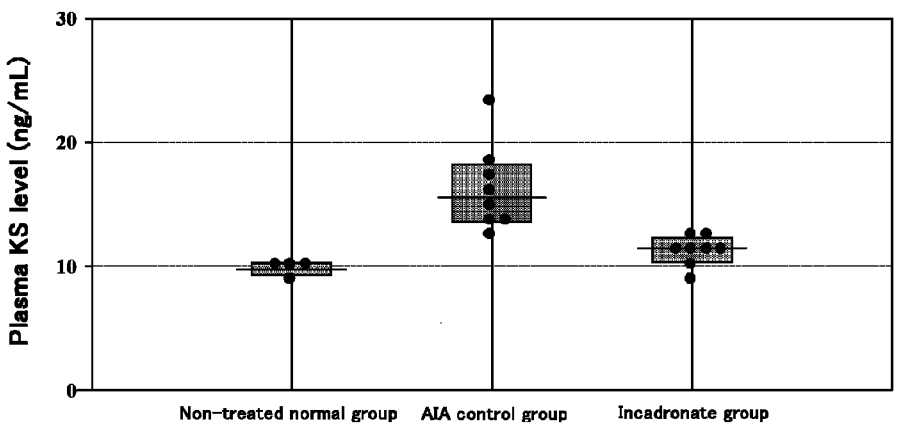
FIG. 8 shows keratan sulfate levels of plasma samples of rats having an adjuvant-induced arthritis.

The plasma KS levels of the AIA model rat groups could not be detected by means of the conventional KS assay kit but could be detected by means of the KS assay system of the present invention. FIG. 8 shows only the results of the assay by means of the KS assay system of the present invention. As is clear from FIG. 8, the plasma KS level of the AIA group was higher than that of the non-treated normal group, which is a profile similar to the edema increase profile. The plasma KS level of the incadronate group is reduced as compared with the AIA control group, which is similar to the edema decrease (amelioration) profile. Thus, the KS assay system of the present invention elucidated that the AIA model rat group exhibited an elevated plasma KS level on 35 day after administration of the adjuvant and that the elevated KS level was lowered through treatment with incadronate. Since the profile of the change in KS level coincides with the edema variation profile, it was revealed that the determination of the plasma KS level of the AIA model rat group through the KS assay system of the present invention enables assessment of joint conditions and evaluation of the effect of the remedy.

As has been known, AIA is a model of chronic rheumatoid arthritis (RA). Therefore, the above experiments have revealed that the method of the present invention enables assessment of RA and the effect of an RA remedy.

Example 6

Determination of Blood KS Level of Papain-Induced Arthritis Model in Rabbit

Figure 9:
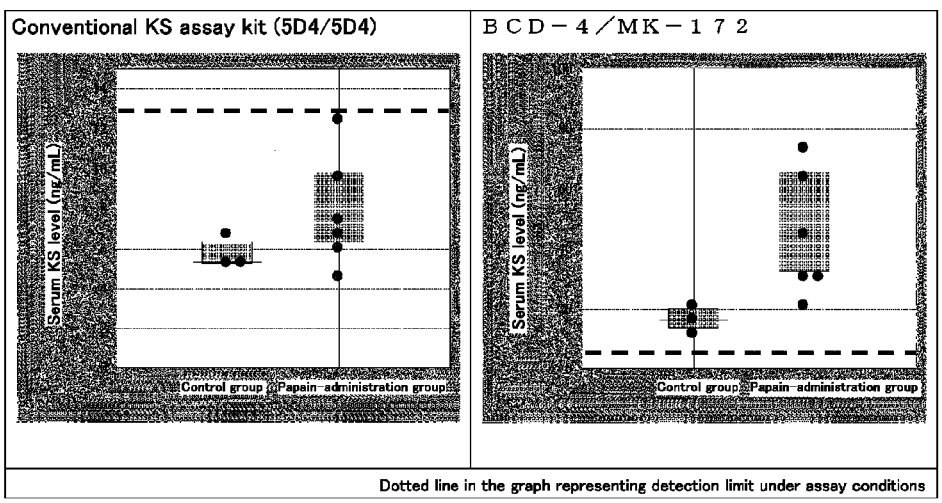
FIG. 9 shows KS levels of serum samples of papain-induced model rabbits.

Papain physiological saline solution (25 mg/mL) (papain, product of SIGMA) was administered to each of the rabbits in the knee joint cavity of the left hindlimb at 150 μL/joint. One week after, an equiamount of the papain solution was administered again. In the control group, physiological saline was administered in a similar manner to the knee joint cavity of the left hindlimb. On day 49 after first administration of papain, blood serum was collected from each rabbit, and the serum KS level was determined. The KS level was determined, by means of a conventional KS assay kit and through the KS assay system of the present invention. In the KS assay system of the present invention, a "solid-phase: BCD-4, detection: HRP-labeled MK-172" system was employed, and the assay was performed in a manner similar to that of Example 2. In the conventional KS assay kit, "solid-phase: 5D4, detection: biotin-labeled 5D4" system was employed. The dilution factor of the rabbit serum was 5 fold (×5 at measurement) in the case of the conventional KS assay kit and 20 fold (×120 at measurement) in the case of the KS assay system of the present invention. FIG. 9 shows the results.

In the assay by means of the conventional KS assay kit, KS levels of most of the 5-fold diluted samples were under the detection limit. Although the KS level of the papain-administered group was slightly higher than that of the control group, satisfactory determination of the KS level was not performed.

In contrast, in the BCD-4/MK-172 system of the present invention, the KS levels of 20-fold diluted rabbit serum samples could be sufficiently detected, and the KS level of the papain-administered group could be clearly evaluated to be higher than that of the control group.

Thus, since the KS assay system of the present invention attains high KS detection sensitivity, it was revealed that such a KS level that a conventional KS assay kit cannot determine can be detected by the KS assay system of the invention, and, variation in KS level of a biological sample can be detected at high sensitivity.

Example 7

Determination of Blood KS Levels of Joint Disease Patients

The serum samples of knee osteoarthritis (OA) patients (n=29), traumatic knee arthropathy (TA) patients (n=17), and healthy subjects (n=18) collected in Referential Example 7 were employed also in Example 7.

Figure 10:
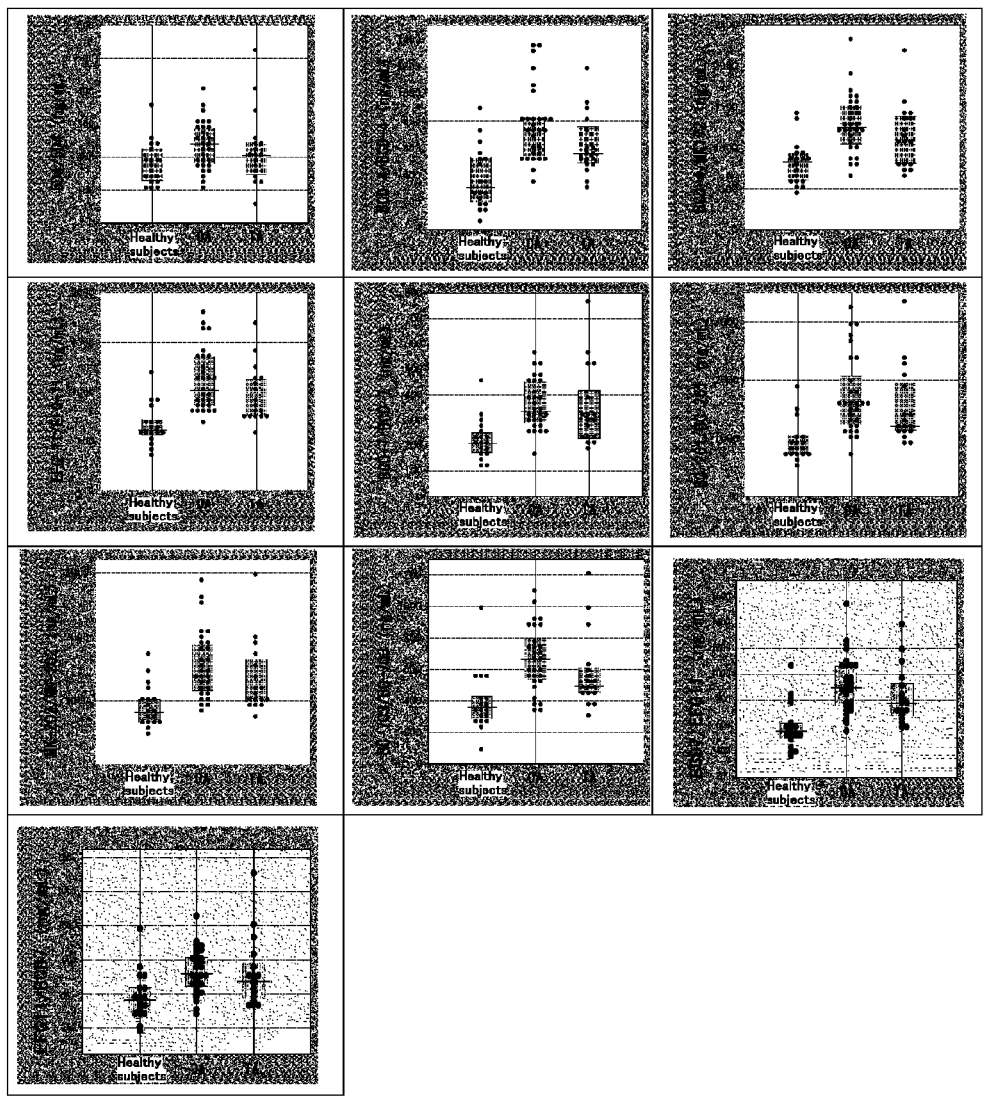
FIG. 10 shows blood KS levels of healthy people groups, OA groups, and TA groups.
Figure 11:
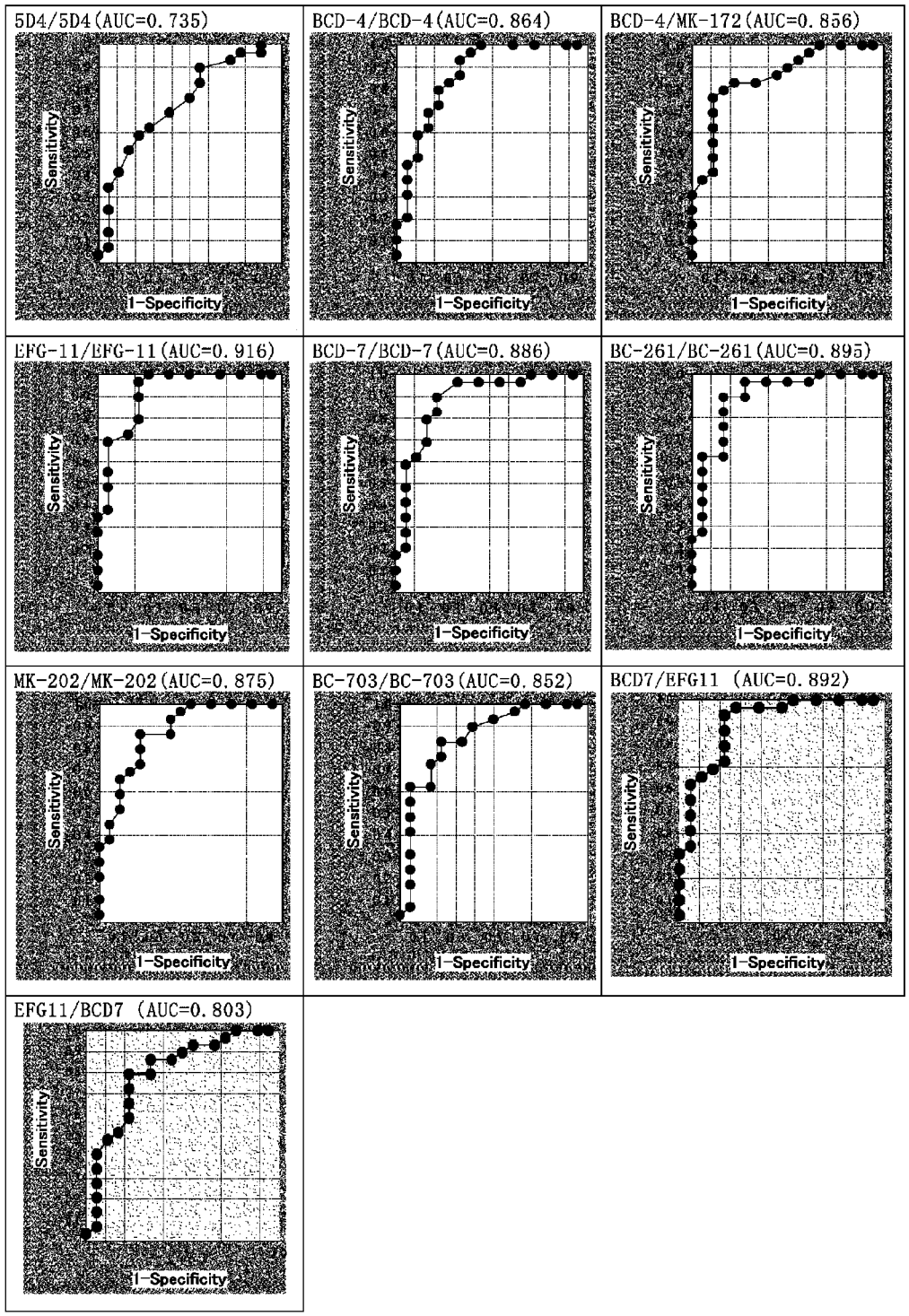
FIG. 11 shows ROC curves of blood KS levels of healthy people groups and OA groups.
Figure 12:
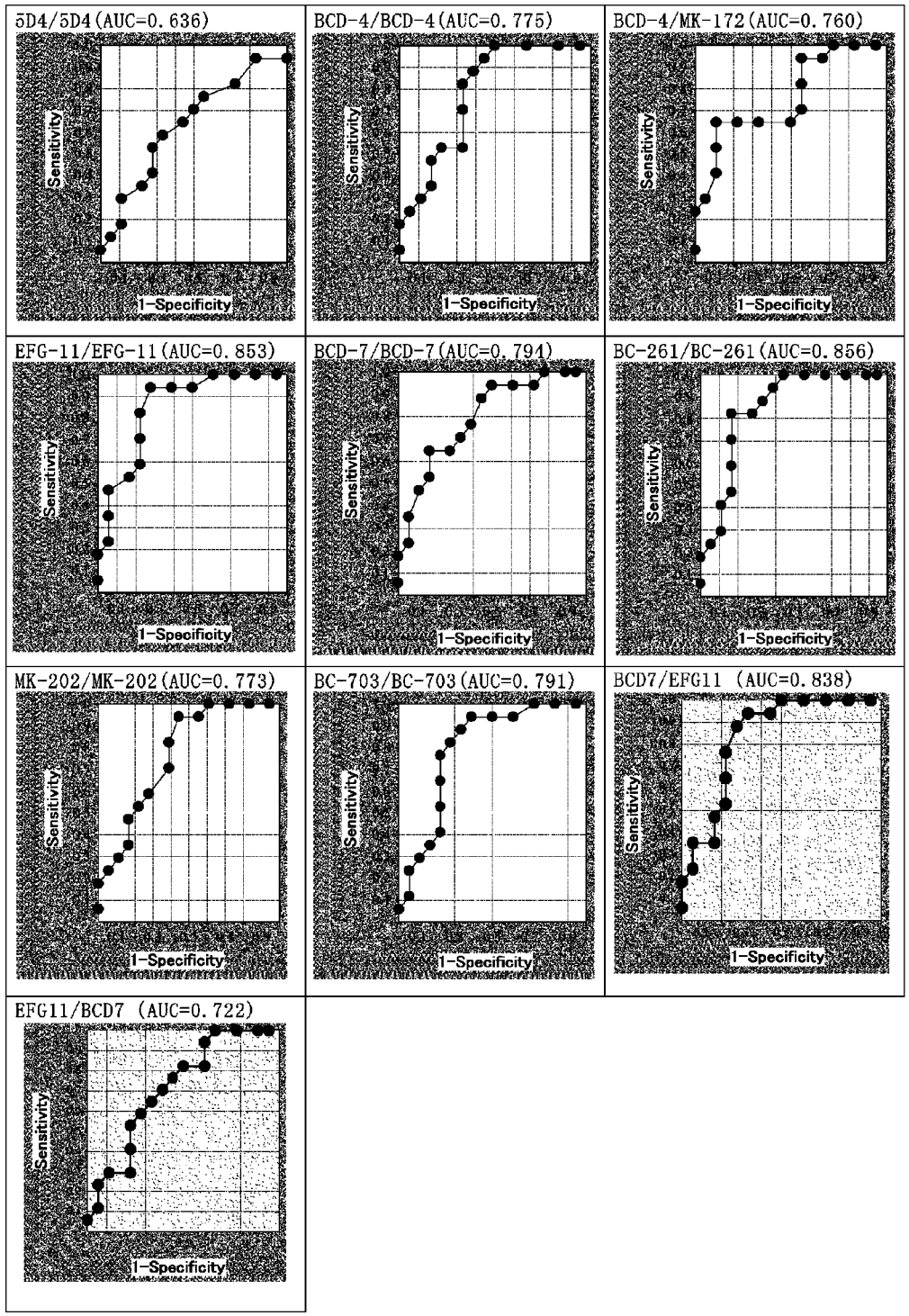
FIG. 12 shows ROC curves of blood KS levels of healthy people groups and TA groups.

The determination was performed by means of a commercial 5D4 KS assay kit or an antibody combination shown in Table 10. The assayed samples had a dilution factor shown in Table 10. The determination through the assay system of the present invention was performed in a manner similar to that employed in Example 2. In each group, the median and quartile deviation (q.d.) were calculated and are shown in Table 11, and the results of determination are shown in the graphs of FIG. 10. The significance test was performed through the Mann-Whitney test with respect to the healthy subjects. In addition, the receiver operating characteristic curves (ROC curve) of each disease group with respect to the healthy subject group were plotted. FIG. 11 shows the assay results of the healthy subject group and the OA group, and FIG. 12 shows the assay results of the healthy subject group and the TA group. The ROC curves were evaluated by area under curve (AUC). AUC has a minimum value of 0.5 and a maximum value of 1.0, the higher the value, and the higher the diagnostic effect.

TABLE 10

| | Dilution factor of samples | |
|---|---|---|
| Solid-phase | Detection | Sample dilution factor |
| 5D4 | 5D4 | ×50 |
| BCD-4 | BCD-4 | ×1000 |
| BCD-4 | MK-172 | ×1000 |
| EFG-11 | EFG-11 | ×800 |
| BCD-7 | BCD-7 | ×150 |
| BC-261 | BC-261 | ×200 |
| MK-202 | MK-202 | ×400 |
| BC-703 | BC-703 | ×150 |

TABLE 11

| | Blood KS levels of the tested groups | | | | | | | |
|---|---|---|---|---|---|---|---|---|
| | Healthy (n = 18) | | OA (n = 29) | | | TA (n = 17) | | |
| | median (ng/mL) | q.d. | median (ng/mL) | q.d. | statistical significance (p value) | median (ng/mL) | q.d. | statistical significance (p value) |
| 5D4/5D4 | 173 | 47.5 | 240 | 54.4 | 0.0073 | 205 | 50.0 | 0.204 |
| BCD-4/BCD-4 | 309 | 166.5 | 744 | 141.0 | 0.00003 | 560 | 135.0 | 0.0056 |

TABLE 11-continued

Blood KS levels of the tested groups

| | Healthy (n = 18) | | OA (n = 29) | | | TA (n = 17) | | |
|---|---|---|---|---|---|---|---|---|
| | median (ng/mL) | q.d. | median (ng/mL) | q.d. | statistical significance (p value) | median (ng/mL) | q.d. | statistical significance (p value) |
| BCD4/MK172 | 830 | 170.5 | 1250 | 245.8 | 0.00005 | 1100 | 291.5 | 0.0087 |
| EFG-11/EFG-11 | 612 | 80.0 | 1016 | 248.0 | 0.000002 | 848 | 190.0 | 0.00036 |
| BCD-7/BCD-7 | 209 | 39.8 | 335 | 80.6 | 0.00001 | 311 | 96.2 | 0.003 |
| BC-261/BC-261 | 822 | 171.0 | 1564 | 423.8 | 0.000007 | 1212 | 406.0 | 0.0003 |
| MK-202/MK202 | 816 | 182.0 | 1448 | 357.0 | 0.00002 | 1108 | 331.5 | 0.0058 |
| BC-703/BC-703 | 359 | 71.3 | 666 | 130.7 | 0.00006 | 492 | 80.3 | 0.0031 |
| BCD7/EFG1 | 556 | 58.0 | 895 | 152.0 | 0.000007 | 770 | 124.9 | 0.00072 |
| EFG11/BCD7 | 363 | 73.0 | 519 | 83.1 | 0.00052 | 472 | 104 | 0.02481 |

(Significance test: vs healthy)

The KS levels (median, ng/mL) determined by means of the conventional KS assay kit (5D4/5D4) were 173 in the healthy subject group, 240 in the OA group, and 205 in the TA group. The KS levels of the OA group and the TA group were higher than the KS level of the healthy subject group. In all the tested antibody combinations, the KS levels of the OA group and the TA group were higher than the KS level of the healthy subject group, which is similar to the case of the conventional KS assay kit. In the tested antibody combinations, the KS levels of the healthy subject group, the OA group, and the TA group were all higher than those determined by means of the conventional KS assay kit.

In the case of the conventional KS assay kit, the statistical significance values (p values) in KS level of the OA group and the TA group with respect to the healthy subject group were 0.0073 and 0.204, respectively, indicating that there was no significant difference between the KS level of the healthy subject group and that of the TA group. In the nine tested antibody combinations, the statistical significance values were lower than those obtained in the case of the conventional assay kit, indicating that the significance of the KS assay of the invention was improved.

In the ROC curves obtained by the conventional KS assay kit (5D4/5D4), the AUC of the KS level of the OA group with respect to the KS level of the healthy subject group was found to be 0.735, and the AUC of the KS level of the TA group with respect to the KS level of the healthy subject group was found to be 0.636. In the nine tested antibody combinations, the AUCs of the KS level of the OA group and the TA group were higher than the AUC obtained by the conventional KS assay kit. Thus, the assay system of the present invention exhibited improved joint disease diagnostic effect as compared with a conventional KS assay kit.

Figure 13:
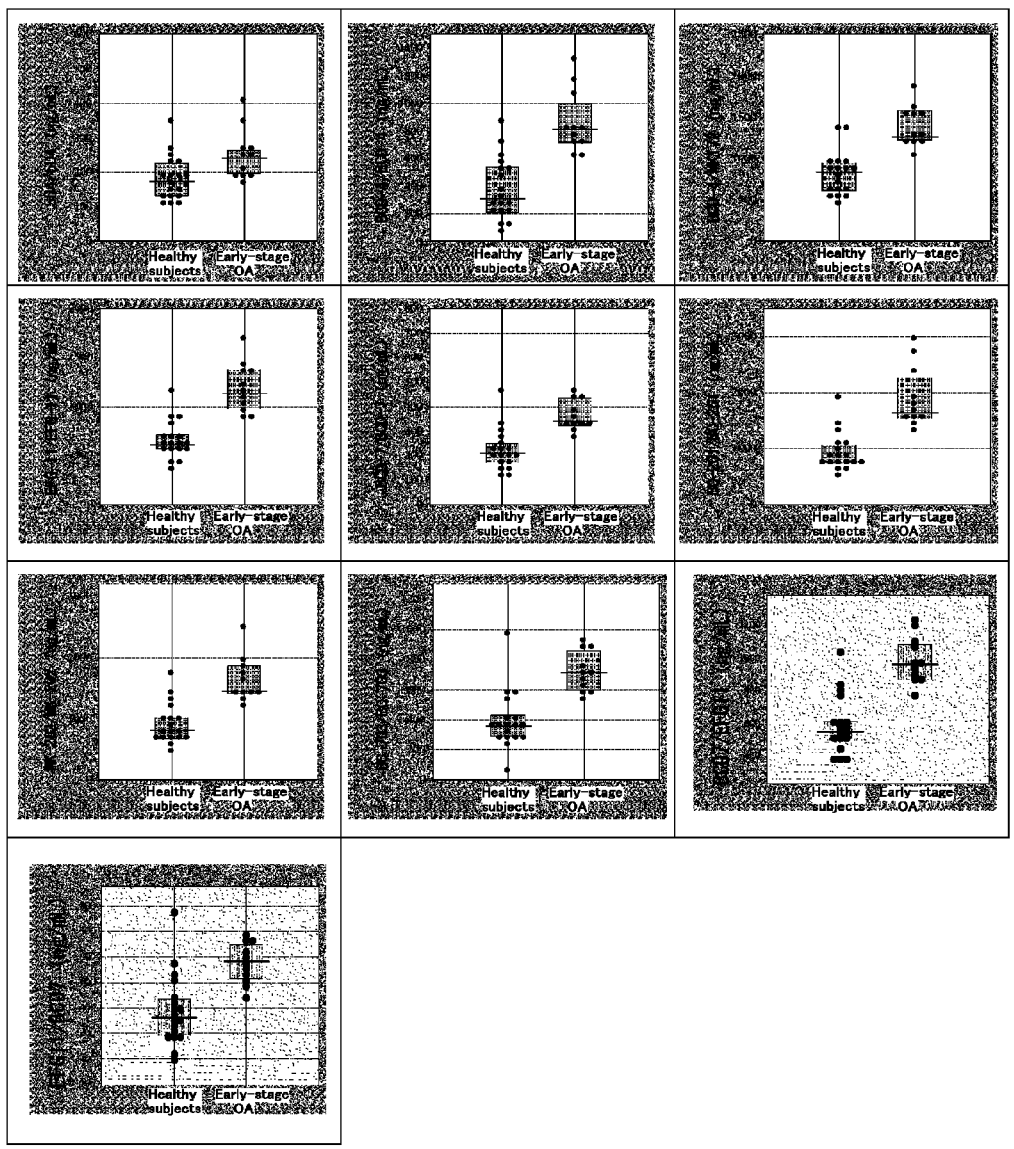
FIG. 13 shows blood KS levels of healthy people groups and early-stage OA groups.
Figure 14:
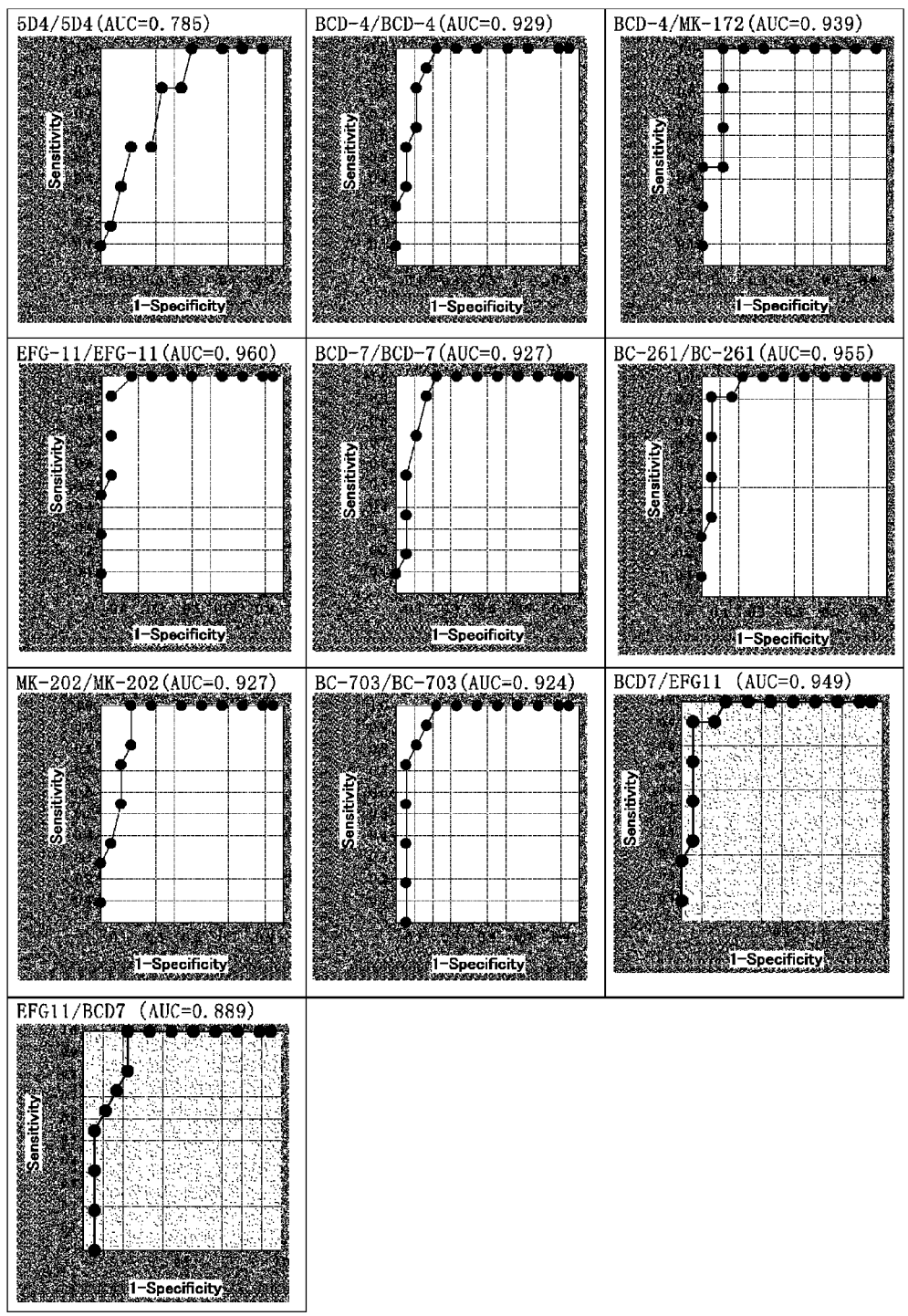
FIG. 14 shows ROC curves of blood KS levels of healthy people groups and early-stage OA groups.

In the OA patient group, the early-stage patients, who have no particular observation in an X-ray examination or whose relevant observation is difficult to detect by an X-ray examination (i.e., grade 0 or grade I) were selected and subjected to the same analysis as described above. Table 12 shows the median and the quartile deviation of each group, and FIG. 13 shows a graph of the results of the assay. FIG. 14 shows the ROC curves of the early-stage OA groups with respect to the healthy subject group.

TABLE 12

Blood KS levels of the tested groups

| | Healthy (n = 18) | | Early-stage OA (n = 11) | | |
|---|---|---|---|---|---|
| | median (ng/mL) | q.d. | median (ng/mL) | q.d. | statistical significance (p value) |
| 5D4/5D4 | 173 | 47.5 | 240 | 34.4 | 0.011 |
| BCD-4/BCD-4 | 309 | 166.5 | 812 | 142.8 | 0.00013 |
| BCD4/MK172 | 830 | 170.5 | 1265 | 177.6 | 0.00009 |
| EFG-11/EFG-11 | 612 | 80.0 | 1136 | 201.0 | 0.00004 |
| BCD-7/BCD-7 | 209 | 39.8 | 342 | 56.1 | 0.00014 |
| BC-261/BC-261 | 822 | 171.0 | 1644 | 361.5 | 0.00005 |
| MK-202/MK202 | 816 | 182.0 | 1448 | 227 | 0.00015 |
| BC-703/BC-703 | 359 | 71.3 | 714 | 130.3 | 0.00016 |
| BCD7/EFG11 | 556 | 58.0 | 966 | 107.8 | 0.00006 |
| EFG11/BCD7 | 363 | 73.0 | 583 | 66.9 | 0.00054 |

(Significance test: vs healthy)

The KS levels (median, ng/mL) determined by means of the conventional KS assay kit (5D4/5D4) were 173 in the healthy subject group and 240 in the early-stage OA group, indicating that the KS level of the early-stage OA group was higher than the KS level of the healthy subject group. Similar to the case of the conventional KS assay kit, in all the tested antibody combinations, the KS levels of the early-stage OA group and the TA group were higher than the KS level of the healthy subject group.

In the case of the conventional KS assay kit, the significance values (p value) in KS level of the early-stage OA group with respect to the healthy subject was 0.011, which is significant. In the nine tested antibody combinations, the p values were considerably lower than those obtained in the case of the conventional KS assay kit, indicating that the significance of the assay of the invention was remarkably improved.

In the ROC curve obtained by the conventional KS assay kit (5D4/5D4), the AUC of the KS level of the early-stage OA group with respect to the healthy subject group was found to be 0.785. In the nine tested antibody combinations, the AUCs of the KS level of the early-stage OA patients were ≥0.85, and were higher than the AUC obtained by the conventional KS assay kit. Thus, the assay system of the present invention exhibited improved early-stage OA diagnostic effect as compared with a conventional KS assay kit.

By virtue of the clinical advantages in assessing a joint disease, the assay system of the present invention was found to serve as a joint disease diagnostic tool which is more powerful than a conventional KS assay kit.

The invention claimed is:

1. A method for immunologically determining a keratan sulfate level, comprising the steps of:(a): contacting a biological sample, simultaneously or sequentially, with a solid phase on which an anti-keratan sulfate monoclonal antibody is immobilized, and with a labeled anti-keratan sulfate monoclonal antibody, to thereby form, on the solid phase, an immune complex of the anti-keratan sulfate antibodies and the keratan sulfate contained in the biological sample;
   (b): detecting a signal produced by the labeled antibody in said immune complex; and
   (c): determining the level of keratan sulfate in said biological sample based on the intensity of said detected signal, wherein said immobilized antibody is BCD-4 and wherein said labeled antibody is labeled MK-172, wherein the biological sample is derived from a rabbit, guinea pig, rat, mouse or human.

2. The keratan sulfate immunological determination method according to claim 1, wherein the biological sample is derived from a rabbit, guinea pig, rat, or mouse.

3. The keratan sulfate immunological determination method according to claim 1, wherein the biological sample is derived from a human.

4. The keratan sulfate immunological determination method according to claim 1, wherein the biological sample is a blood sample or synovial fluid.

5. The keratan sulfate immunological determination method according to claim 1, wherein the biological sample has been treated with a protease.

6. The keratan sulfate immunological determination method according to claim 5, wherein the protease is one or more members selected from the group consisting of pronase, subtilisin, papain, and trypsin.

7. A keratan sulfate assay kit for use in a keratan sulfate immunological determination method as recited in claim 3, wherein said kit contains BCD-4 and labeled MK-172 antibodies.

* * * * *